United States Patent [19]
Moberg et al.

[11] Patent Number: 5,496,361
[45] Date of Patent: Mar. 5, 1996

[54] SYSTEM AND METHOD FOR DETECTING CARDIAC ARRHYTHMIAS USING A CARDIAC WALL ACCELERATION SENSOR SIGNAL

[75] Inventors: Sheldon B. Moberg, Kagel Canyon; James D. Causey, III, Simi Valley, both of Calif.

[73] Assignee: Pacesetter, Inc., Sylmar, Calif.

[21] Appl. No.: 278,346

[22] Filed: Jul. 21, 1994

Related U.S. Application Data

[62] Division of Ser. No. 91,636, Jul. 14, 1993.

[51] Int. Cl.$^6$ ............................................. A61N 1/39
[52] U.S. Cl. ............................................. 607/122; 128/642
[58] Field of Search ............................................. 128/642, 698, 128/714, 782; 607/9, 19–20, 23–24, 119, 122, 129

[56] References Cited

U.S. PATENT DOCUMENTS

| | | | |
|---|---|---|---|
| 4,140,132 | 2/1979 | Dahl | 128/419 PG |
| 4,428,378 | 1/1984 | Anderson et al. | 128/419 PG |
| 4,662,377 | 5/1987 | Heilman et al. | 128/419 D |
| 4,686,988 | 8/1987 | Sholder | 128/419 PT |
| 4,712,555 | 12/1987 | Thornander | 128/419 PG |
| 4,774,950 | 10/1988 | Cohen | 128/419 D |
| 4,790,317 | 12/1988 | Davies | 128/419 D |
| 4,821,723 | 4/1989 | Baker, Jr. et al. | 128/419 D |
| 4,936,304 | 6/1990 | Kresh et al. | 128/419 PG |
| 4,967,748 | 11/1990 | Cohen | 128/419 D |
| 4,989,602 | 2/1991 | Sholder et al. | 128/419 D |
| 5,014,697 | 5/1991 | Pless et al. | 128/419 D |
| 5,014,700 | 5/1991 | Alt | 128/419 PG |
| 5,031,615 | 7/1991 | Alt | 128/419 PG |
| 5,040,534 | 8/1991 | Mann et al. | 128/419 PG |
| 5,044,366 | 9/1991 | Alt | 128/419 PG |
| 5,109,842 | 5/1992 | Adinolfi | 607/9 |
| 5,304,208 | 4/1994 | Inguaggiato et al. | 607/17 |
| B1 4,232,679 | 5/1988 | Schulman | 128/419 PG |

OTHER PUBLICATIONS

Atochem Sensors, Inc. Product Brochure, *Standard and Custom Piezo Film Components*, pp. 1–10 (1991).
Bacharach, David W. et al., "Activity–Base Pacing: Comparison of a Device Using an Accelerometer Versus a Piezoelectric Crystal," *Pace*, vol. 15, pp. 188–196 (Feb. 1992).
Piezo Electric Products, Inc., "Piezoceramic Design Notes," *Sensors* (Mar. 1984).
Salerno, David M. et al., "Seismocardiography: A New Technique for Recording Cardiac Vibrations. Concept, Method, and Initial Observations," *Journal of Cardiovascular Technology*, vol. 9, No. 2, 1990, pp. 111–118.
Salerno, David M. et al., "Seismocardiography for Monitoring Changes in Left Ventricular Function During Ischemia," *Chest*, vol. 100, pp. 991–993 (Oct. 1991).
Salerno, David M. et al., "Seismocardiographic Changes Associated With Obstruction of Coronary Blood Flow During Balloon Angioplasty," *The American Journal of Cardiology*, vol. 68, pp. 201–207 (Jul. 15, 1991).
Sandler, H. et al., "Miniature Implantable Accelerometers," pp. 165–174.

*Primary Examiner*—William E. Kamm
*Assistant Examiner*—Marianne Parker
*Attorney, Agent, or Firm*—Lisa P. Weinberg

[57] ABSTRACT

Implantable leads incorporating accelerometer-based cardiac wall motion sensors, and a method of fabricating such leads, are provided. The cardiac wall motion sensors transduce accelerations of cardiac tissue to provide electrical signals indicative of cardiac wall motion to an implantable cardiac stimulating device. The implantable cardiac stimulating device may use the electrical signals indicative of cardiac wall motion to detect and discriminate among potentially malignant cardiac arrhythmias. In response to a detected abnormal cardiac rhythm, the cardiac stimulating device may deliver therapeutic electrical stimulation to selected regions of cardiac tissue.

16 Claims, 9 Drawing Sheets

NORMAL SINUS RHYTHM

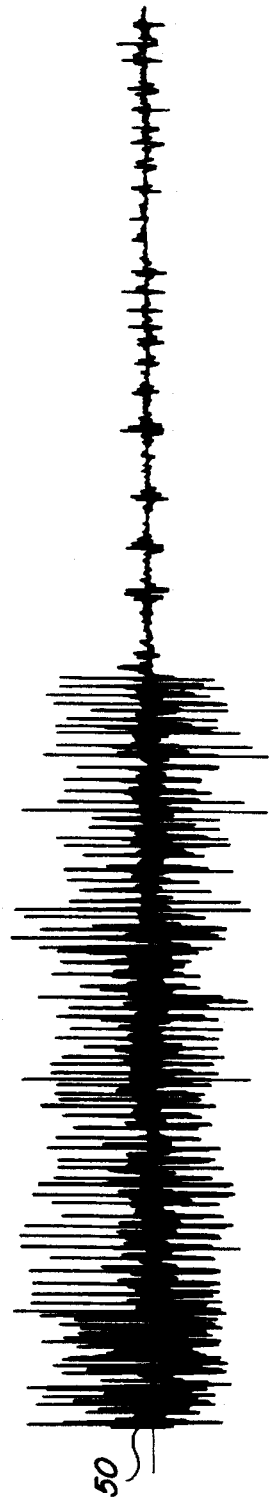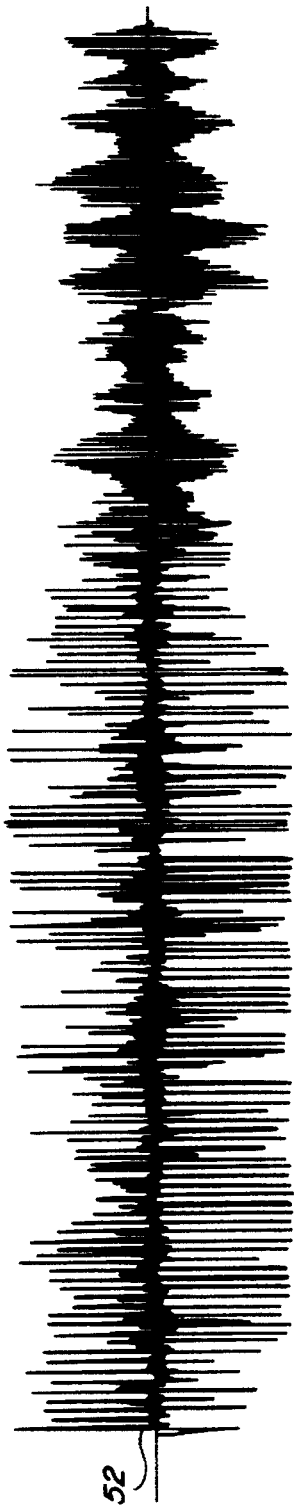
FIG. 2

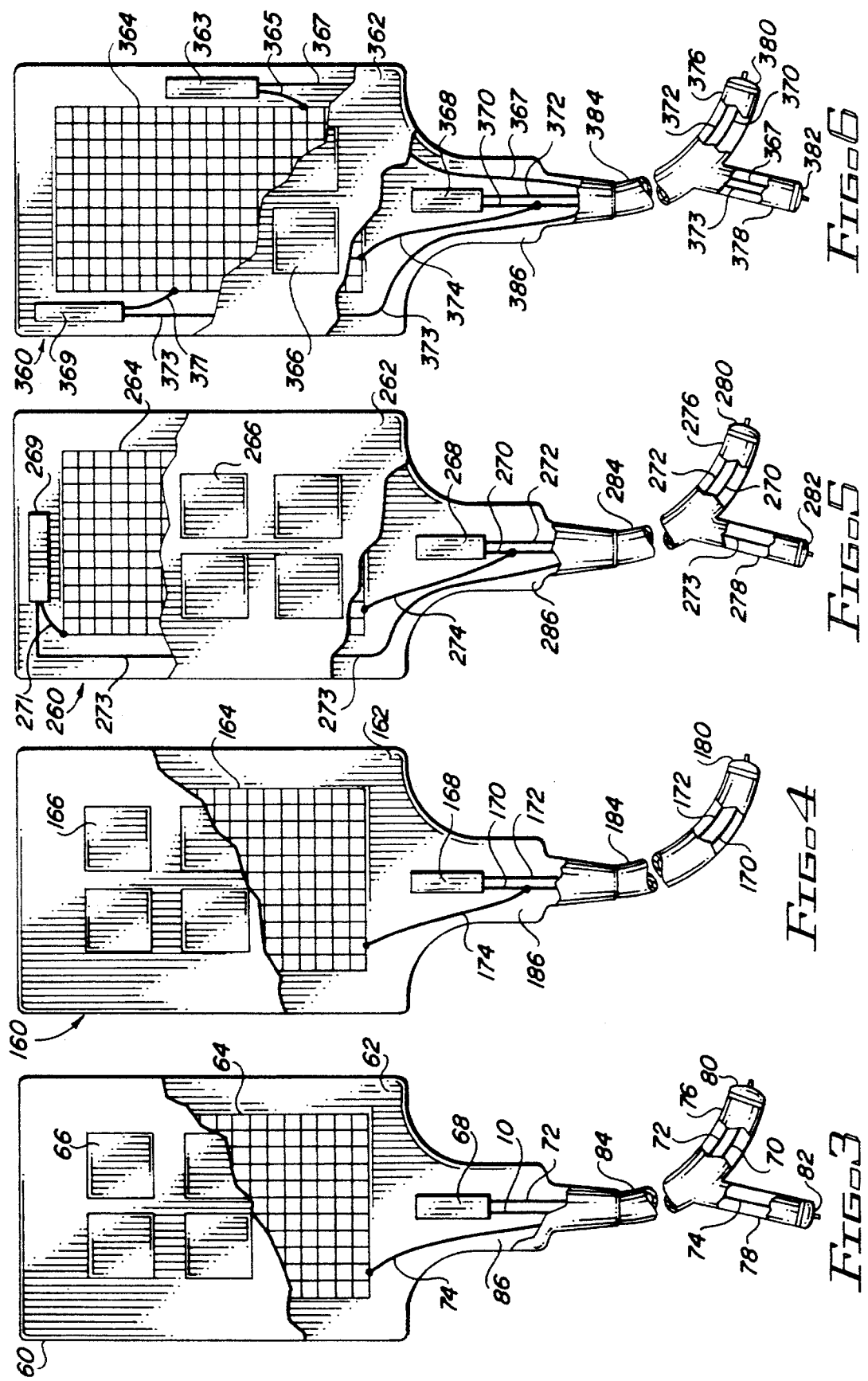

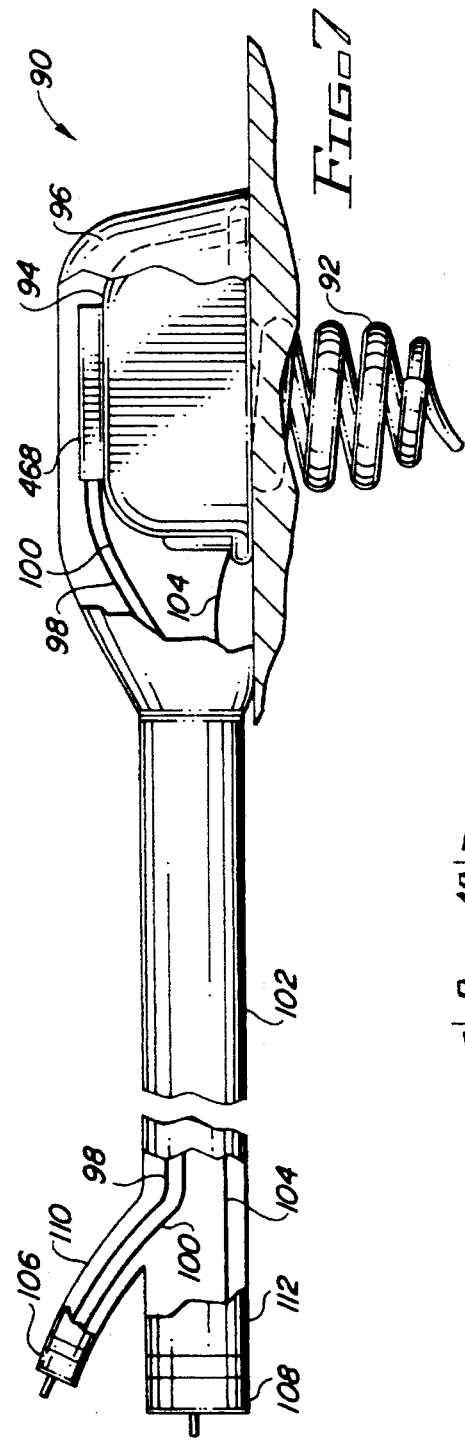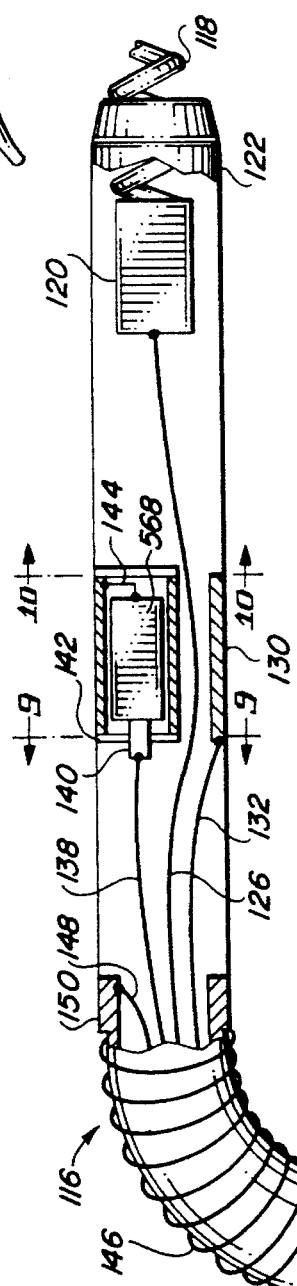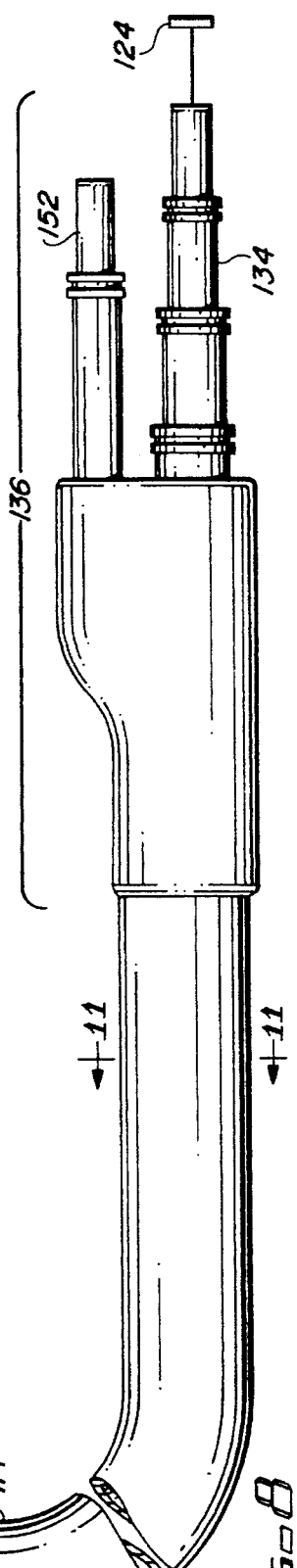

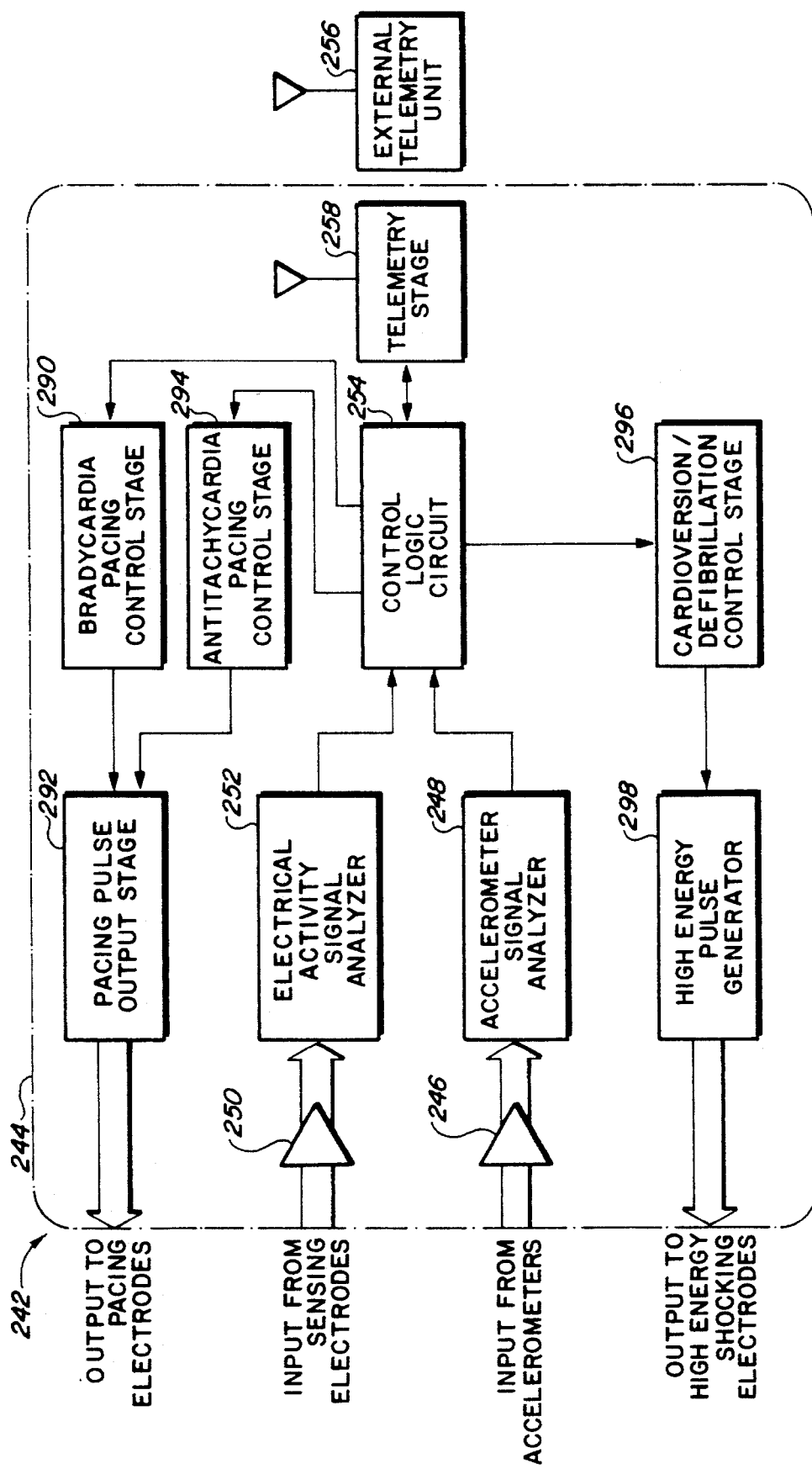

SYSTEM AND METHOD FOR DETECTING CARDIAC ARRHYTHMIAS USING A CARDIAC WALL ACCELERATION SENSOR SIGNAL

This is a divisional of application Ser. No. 08/091,636, filed on Jul. 14, 1993, pending.

BACKGROUND OF THE INVENTION

This invention relates to cardiac stimulating devices and particularly to implantable cardiac stimulating devices, including implantable cardiac pacemakers and implantable cardiac defibrillators, as well as implantable cardioverters and cardioverter/defibrillators. More particularly, this invention relates to implantable leads for such cardiac stimulating devices, which incorporate cardiac wall motion sensors that provide signals indicative of cardiac mechanical activity.

Implantable cardiac stimulating devices for providing therapy in response to a variety of pathological cardiac arrhythmias are known. For example, an implantable cardiac stimulating device may be capable of detecting a pathological cardiac arrhythmia, and responding to the detected arrhythmia by providing therapeutic electrical stimulation. Implantable cardiac stimulating devices may be capable of providing "tiered therapy," in which the type of electrical stimulation provided by the device is determined in accordance with the severity of the arrhythmia, with more aggressive therapies being applied in response to more severe arrhythmias. For example, an implantable cardiac stimulating device may respond to a relatively less severe occurrence of tachycardia by delivering antitachycardia pacing pulses of about 25 microjoules to about 30 microjoules in a sequence known to interrupt such an arrhythmia. In response to a relatively more severe occurrence of tachycardia, the implantable cardiac stimulating device may deliver a low energy shock on the order of about 2 joules to about 5 joules, either in combination with, or as an alternative to, antitachycardia pacing pulses. In response to an occurrence of an even more severe arrhythmia, for example, ventricular fibrillation, the implantable cardiac stimulating device may deliver a high energy "defibrillation" shock on the order of about 10 joules to about 40 joules.

Implantable cardiac stimulating devices for providing pacing pulses to cardiac tissue to maintain a heart rate at a physiologically acceptable rate (i.e.—to provide "bradycardia pacing support") are also known. Bradycardia pacing support may be provided by a dedicated pacemaker, or by a device that is also capable of providing other forms of therapy, such as tiered therapy.

Effective delivery of therapy from an implantable cardiac stimulating device depends upon accurate measurement of intrinsic cardiac activity. In the case of an implantable cardiac stimulating device capable of providing tiered therapy, the device must not only be capable of detecting the onset of an arrhythmia, but must also be capable of discriminating among various types of arrhythmias in order to deliver an appropriate form of electrical stimulation therapy. For example, if ventricular fibrillation is incorrectly diagnosed by the device as a relatively less severe arrhythmia, valuable time may be lost if an inappropriate, less aggressive therapy, such as antitachycardia pacing, is applied. If tachycardia is incorrectly diagnosed as ventricular fibrillation, the patient may consciously experience high energy defibrillation shocks, which may be ineffective in terminating the tachycardia, in addition to being extremely uncomfortable.

Measurement of intrinsic cardiac activity is also desirable for implantable cardiac stimulating devices capable of providing bradycardia pacing support. Typically, the delivery of bradycardia pacing pulses from such devices is inhibited by spontaneous, hemodynamically effective, cardiac contractions occurring at a predetermined rate. For example, if the intrinsic heart rate of a patient during a particular time interval is greater than a predetermined threshold rate, delivery of pacing pulses may be inhibited during that time interval. Pacing pulses would be provided when the intrinsic heart rate falls below the threshold rate. Pacing pulse inhibition is desirable because it extends battery life by avoiding delivery of unnecessary stimulation pulses. In order for a device to be capable of inhibiting delivery of pacing pulses, it must be capable of detecting intrinsic cardiac activity.

Many implantable cardiac stimulating devices that detect and discriminate among cardiac arrhythmias monitor heart rate, which is usually accomplished by measuring cardiac electrical activity—i.e., the intercardiac electrogram (IEGM). The IEGM is typically sensed by electrodes that are also used to deliver electrical stimulation therapy to the cardiac tissue. However, under many circumstances, it is difficult to sense the IEGM. For example, the device may not be able to discern the IEGM over noise or other physiological electrical activity, or perhaps even external interference. As a result, an implantable cardiac stimulating device may have difficulty detecting the onset of an arrhythmia. As another illustration, implantable cardiac stimulating devices capable of providing bradycardia pacing support may be inhibited from sensing cardiac electrical activity during a period of time immediately following the delivery of a pacing pulse, due to the presence of a pulse-induced afterpotential.

Other known implantable cardiac stimulating devices use hemodynamic signals to detect cardiac arrhythmias. For example, U.S. Pat. No. 4,774,950 to Cohen refers to a system that may detect cardiac arrhythmias by measuring mean pressure at a variety of locations (e.g., mean arterial pressure, mean right ventricle pressure, mean left atrial pressure, mean left ventricle pressure or mean central venous pressure). For a selected mean pressure, a short term current mean pressure is compared to a long term mean baseline pressure, and if they differ by a predetermined valve, the patient may be deemed to be experiencing a cardiac arrythmia. The mean pressure data may also be used in combination with heart rate measurements to detect arrhythmias.

Another example of a device that uses hemodynamics to detect cardiac arrhythmias is described in U.S. Pat. No. 4,967,748 of Cohen. In that patent, blood oxygen level is measured at a particular site in the circulatory system of a patient. A comparison is made between a short term sensed blood oxygen level and a baseline blood oxygen level, and if they differ, the patient may be deemed to be experiencing a cardiac arrhythmia.

Unfortunately, the use of hemodynamic indicators such as mean pressure and blood oxygen level may have certain associated drawbacks. One possible drawback is that hemodynamic indicators may not respond rapidly to the onset of an arrhythmia. Thus, an implantable cardiac stimulating device that relies on such hemodynamic signals to detect cardiac arrhythmias may not deliver therapy as rapidly as desired.

In view of the deficiencies associated the use of the IEGM or certain hemodynamic indicators, it would be desirable to provide an improved sensor for detecting and discriminating among various cardiac arrhythmias, and for determining the intrinsic heart rate of a patient. Ideally, such a sensor would provide a signal that rapidly responds to the onset of an arrhythmia, and is not subject to electrical interference from external sources or from pacemaker-induced after potentials.

SUMMARY OF THE INVENTION

The present invention is directed to implantable leads for an implantable cardiac stimulating device, which incorporate cardiac wall motion sensors that provide signals indicative of cardiac mechanical activity. Broadly, the implantable leads of the present invention include a carrier that is adapted for contacting cardiac tissue, a cardiac wall motion sensor delivered to cardiac tissue by the carrier, and a connector that connects the carrier to an implantable cardiac stimulating device. The carrier typically includes conductors disposed therein for conducting the signal provided by the cardiac wall motion sensor to the implantable cardiac stimulating device.

The implantable leads of the present invention may be provided in a number of configurations, depending upon the needs of a particular patient. For example, a cardiac wall motion sensor may be disposed within a flexible patch, a myocardial active-fixation lead, an endocardial lead, or other leads suitable for use with an implantable cardiac stimulation device. A myocardial active-fixation lead is disclosed in copending application entitled "Implantable Myocardial Stimulation Lead with Sensors Thereon," filed concurrently herewith, which is hereby incorporated herein by reference. Although the implantable leads of the present invention typically include an electrode for delivering therapeutic electrical stimulation to cardiac tissue, a cardiac wall motion sensor may be delivered to cardiac tissue by a dedicated cardiac wall motion sensor lead. A dedicated cardiac wall motion sensor lead may be advantageous when it is desirable to measure cardiac wall motion at a region remote from the cardiac tissue locations intended to receive electrical stimulation.

In a preferred embodiment, the implantable leads of the present invention incorporate one or more cardiac wall motion sensors that are accelerometer-based. The cardiac wall motion sensors transduce accelerations of cardiac tissue to which the leads are attached, so as to provide one or more signals indicative of cardiac mechanical activity. Preferably, the cardiac wall motion sensors of the present invention are sensitive to accelerations along at least two perpendicular axes, and may be sensitive to accelerations along three perpendicular axes.

In another aspect of the invention, a method of fabricating implantable leads incorporating cardiac wall motion sensors is provided. The method of the present invention may be used to fabricate leads in a variety of configurations, depending on the needs of a particular patient.

The present invention also provides an implantable system that uses a signal provided by a cardiac wall motion sensor delivered to cardiac tissue by an implantable lead, to detect and discriminate among various cardiac arrhythmias. The implantable system of the present invention applies therapeutic electrical stimulation to cardiac tissue when a cardiac arrhythmia is detected. The signal from the cardiac wall motion sensor may be used by the implantable system as a primary indicator of potentially malignant cardiac arrhythmias. Alternatively, the cardiac wall motion sensor signal may be used by the implantable system in combination with, for example, conventional R-wave detection circuitry that relies on an IEGM for measuring cardiac activity. In either mode, the use of output from a cardiac wall motion sensor of the present invention overcomes known difficulties associated with relying solely on an IEGM for detecting and discriminating among various cardiac arrhythmias.

The system of the present invention that uses a signal provided by a cardiac wall motion sensor to detect and discriminate among cardiac arrhythmias operates based on knowledge that cardiac wall motion associated with normal sinus rhythm follows a regular, identifiable pattern. Cardiac wall motion associated with potentially malignant arrhythmias, such as tachycardia or ventricular fibrillation, is typically rapid, chaotic or both. In a patient experiencing bradycardia, cardiac wall motion is not rapid or chaotic, but is typically distinguishable from cardiac wall motion associated with normal sinus rhythm. By affixing an implantable lead incorporating a cardiac wall motion sensor to selected regions of cardiac tissue, cardiac wall motion is experienced and transduced by the sensor, and the resulting signal may be used by the implantable system of the present invention to distinguish between normal and pathological cardiac rhythms, and to discriminate among various known arrhythmias.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 2 is a graph of a signal from a cardiac wall motion sensor disposed on a myocardial patch electrode attached to left ventricular myocardial tissue, a surface electrocardiogram and an aortic pressure signal, all plotted versus time, each indicative of a subject transitioning from tachycardia to ventricular fibrillation;

FIG. 3 is a partial cutaway view of a preferred embodiment of a flexible patch electrode having a two-terminal bifurcated lead and incorporating a cardiac wall motion sensor in accordance with the principles of the present invention;

FIG. 4 is a partial cutaway view of another preferred embodiment of a flexible patch electrode having a one-terminal in-line lead and incorporating a cardiac wall motion sensor in accordance with the principles of the present invention;

FIG. 5 is a partial cutaway view of another preferred embodiment of a flexible patch electrode having a two-terminal bifurcated lead and incorporating two cardiac wall motion sensors in accordance with the principles of the present invention;

FIG. 6 is a partial cutaway view of another preferred embodiment of a flexible patch electrode having a three-terminal bifurcated lead and incorporating three cardiac wall motion sensors in accordance with the principles of the present invention;

FIG. 7 is a partial cutaway view of a preferred embodiment of a myocardial active-fixation lead incorporating a cardiac wall motion sensor in accordance with the principles of the present invention;

FIG. 8 is a partial cutaway view of a preferred embodiment of an endocardial lead incorporating a cardiac wall motion sensor in accordance with the principles of the present invention;

FIG. 18 is a schematic block diagram of an implantable cardiac stimulating device constructed in accordance with the principles of the present invention;

DETAILED DESCRIPTION OF THE PREFERRED EMBODIMENTS

Figure 1:
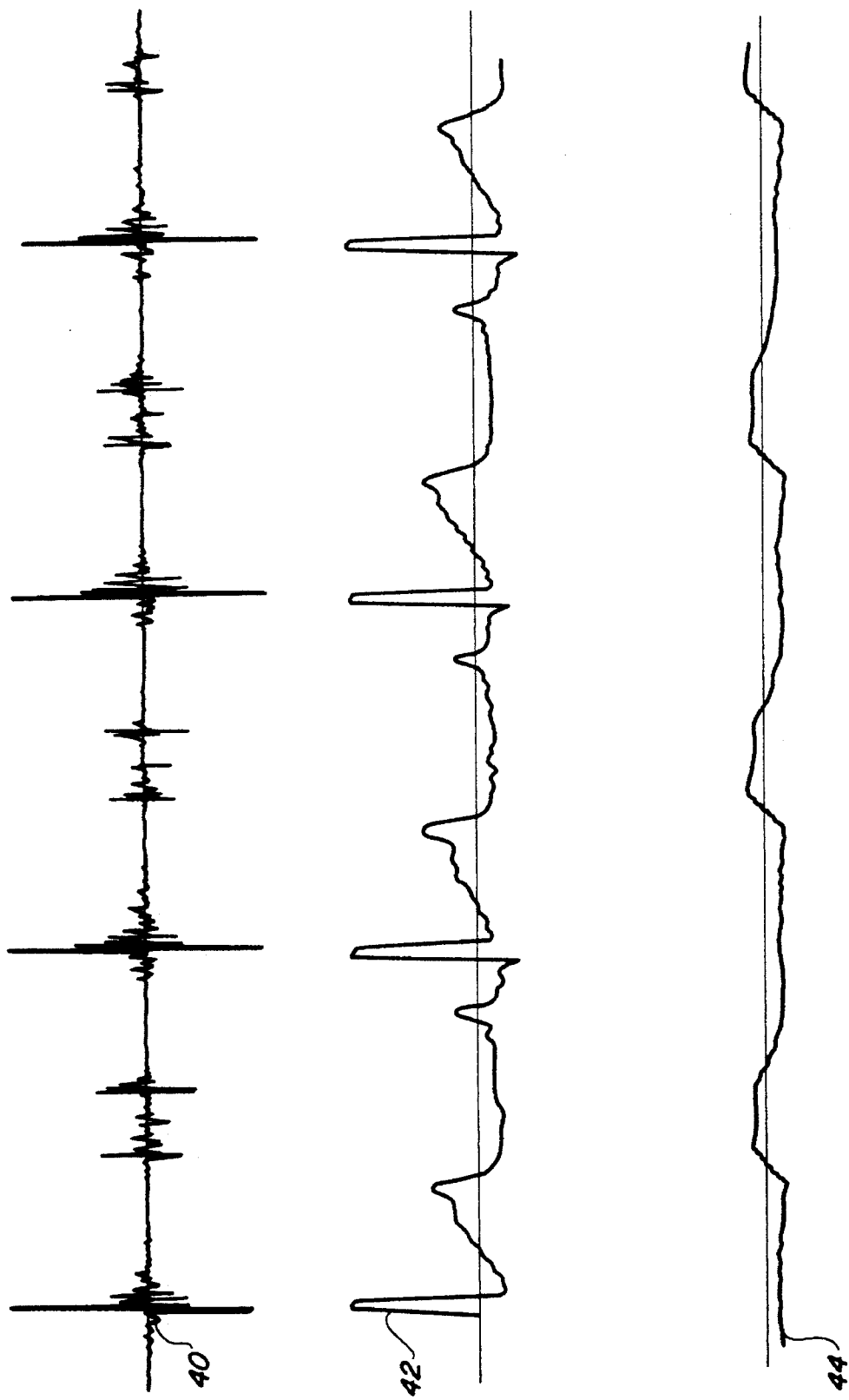
FIG. 1 is a graph of a signal from a cardiac wall motion sensor disposed within an endocardial lead attached to right ventricular endocardial tissue, a surface electrocardiogram and an aortic pressure signal, all plotted versus time, each indicative of a subject in normal sinus rhythm.

Referring to FIGS. 1 and 2, two cardiac wall motion sensor signals 40 and 50 provided from two cardiac wall motion sensors (not shown; described below) in accordance with the principles of the present invention are described and compared to two electrocardiograms 42 and 52 and two aortic pressure signals 44 and 54. In FIG. 1, the cardiac wall motion sensor signal 40, the electrocardiogram 42 and the aortic pressure signal 44 were recorded at a chart speed of 100 mm/sec from a subject in normal sinus rhythm. An accelerometer-based cardiac wall motion sensor disposed within an endocardial lead (not shown; described below) was used to provide the cardiac wall motion sensor signal 40. In FIG. 2, the cardiac wall motion sensor signal 50, the electrocardiogram 52 and the aortic pressure signal 54 were recorded at a chart speed of 5 mm/sec from a subject transitioning from an epinephrine-induced tachycardia into ventricular fibrillation. An accelerometer-based cardiac wall motion sensor disposed on a patch electrode (not shown) was used to provide the cardiac wall motion sensor signal 50.

As shown in FIG. 1, the cardiac wall motion sensor signal 40 from a subject in normal sinus rhythm exhibits relatively low frequency amplitude fluctuations that are substantially periodic. FIG. 2 shows that the cardiac wall motion sensor signal 50 from a subject experiencing tachycardia is chaotic, and that the frequency is relatively high. Upon the onset of ventricular fibrillation, the amplitude of the signal fluctuations substantially decreases, while the frequency remains relatively high.

Transitions in the cardiac wall motion sensor signals 40 and 50 are coincident with transitions in the electrocardiograms 42 and 52 and the aortic pressure signals 44 and 54. Thus, it is shown that the cardiac wall motion sensor signals 40 and 50 may be used to discriminate among various cardiac arrhythmias in a manner traditionally accomplished by analyzing the electrocardiograms 42 and 52 or the aortic pressure signals 44 and 54. An implantable cardiac stimulating device (not shown; described below) may be constructed to receive a cardiac wall motion sensor signal (which is indicative of cardiac mechanical activity) and an IEGM (which is indicative of cardiac electrical activity), and may be configured to use either form of information, or both forms of information in combination, to detect and discriminate among various types of cardiac arrhythmias and to determine intrinsic heart rate.

A cardiac wall motion sensor in accordance with the principles of the present invention (which is preferably accelerometer-based) may be delivered and affixed to cardiac tissue using a variety of leads known to be suitable for use with an implantable cardiac stimulating device. The described embodiments of the present invention are merely illustrative examples of such leads, and the principles of the present invention may be applied to other suitably configured leads. For instance, when it is desirable to measure cardiac wall motion at regions remote from areas normally contacted by a stimulating lead, a dedicated cardiac wall motion sensor lead may be used.

Referring now to FIG. 3, a preferred embodiment of a flexible epicardial patch electrode incorporating a cardiac wall motion sensor suitable for use with an implantable cardiac stimulating device is described. An epicardial patch electrode 60 includes an electrically conductive wire mesh 64 substantially enclosed within a carrier 62. Preferably, the wire mesh 64 is made from titanium wire or a titanium sheet, and the carrier 62 is made from silicone sheeting reinforced with synthetic polyester fibers (commonly known by the trademark DACRON, owned by E. I. du Pont de Nemours & Company). The side of the carrier 62 that is intended for contact with a region of the cardiac wall (not shown) includes a plurality of windows 66, as shown in FIG. 3. The windows 66 permit the wire mesh 64 to make electrical contact with a region of the cardiac wall when the patch electrode 60 is sutured to the epicardium (not shown), so that the patch electrode 60 can deliver therapeutic electrical stimulation when so required.

The patch electrode 60 further includes a cardiac wall motion sensor 68 embedded therein. When the patch electrode 60 is sutured to the epicardium, the cardiac wall motion sensor 68 will experience the motion of a region of the cardiac wall to which the patch electrode 60 is attached. Motion experienced by the cardiac wall motion sensor 68 will cause the cardiac wall motion sensor 68 to generate an electrical signal that is indicative of the motion of a region of the cardiac wall. Preferably, the cardiac wall motion sensor 68 is within a hermetically sealed enclosure.

The cardiac wall motion sensor 68 is electrically connected to an implantable cardiac stimulating device (not shown) by two wires 70 and 72, which extend to the neck region 86 of the patch electrode 60 via the insulated cable 84. The wire mesh 64 is electrically connected to the implantable cardiac stimulating device by a wire 74, which is also conducted to the neck region 86 of the patch electrode 60 via the insulated cable 84. Preferably, the wires 70, 72 and 74 are drawn-brazed-stranded (DBS) wire, and the cable 84 is coated with polytetrafluoroethylene (commonly known by the trademark TEFLON, owned by E. I. du Pont de Nemours & Company). The insulated cable 84 divides into a branch 76 having a connector 80 for wires 70 and 72, and a branch 78 having a connector 82 for wire 74.

Standard electrical bipolar and unipolar connectors may be used as the connectors 80 and 82, respectively, which provide mechanical and electrical connections to the implantable cardiac stimulating device. The connectors 80 and 82 advantageously provide superior electrical isolation between the cardiac wall motion sensor 68 and the shocking electrode (windows 66 and wire 74) and also offer ease of construction. While the preferred embodiment is shown as having separate or bifurcated connectors 80 and 82, a tripolar in-line connector is also possible. For a complete description of the multipolar in-line connectors which could be used as multipolar terminals, see commonly-assigned U.S. patent application Ser. No. 07/894,395, filed Jun. 5, 1992, to Edward Chernoff, Harry W. Fletcher, Jeryle L. Walter, and James E. Barcel, entitled "Multipolar In-Line Proximal Connector Assembly for an Implantable Stimulation Device," which is incorporated by reference in its entirety.

The size and position of the cardiac wall motion sensor 68, as depicted schematically in FIG. 3, are illustrative, and it is possible to vary the size and position of the cardiac wall motion sensor 68 in order to meet the needs of a particular application. However, the cardiac wall motion sensor 68 should be oriented within the patch electrode 60 so as to be sensitive to cardiac wall motion. The orientation is thusly dependant upon the intended region of the cardiac wall to which the patch electrode 60 is to be attached. When one cardiac wall motion sensor 68 is incorporated into the patch electrode 60, it will preferably be disposed in the neck region 86 as shown in FIG. 3. Preferably, the cardiac wall motion sensor 68 is adhesively secured to either of the two interior surfaces of the carrier 62 with a biocompatible silicone.

Referring now to FIG. 4, another embodiment of an epicardial patch electrode 160 incorporating a single cardiac wall motion sensor 168 is described. The patch electrode 160 is constructed in a similar manner as the patch electrode 60 of FIG. 3. For example, a carrier 162 includes a wire mesh 164, which may contact a region of the cardiac wall (not shown) through a plurality of windows 166 formed on one side of the carrier 162. The patch electrode 160 further includes a cardiac wall motion sensor 168, which is located in a neck region 186 of the carrier 162. The cardiac wall motion sensor 168 is connected to a connector 180 by two wires 170 and 172 which extend through an insulated cable 184.

In this embodiment, a wire 174 that is used to connect the wire mesh 164 to an implantable cardiac stimulating device (not shown) is shared with the cardiac wall motion sensor 168. Instead of using an additional connector, the wire 174 is connected to the wire 170 in the vicinity of the cardiac wall motion sensor 168. This embodiment offers several structural advantages over the one described with respect to FIG. 3. For example, the number of electrical connectors is reduced from two to one. In addition, branching of the cable 184 is avoided. Furthermore, the number of wires in the cable 184 is advantageously reduced from three to two. However, when this configuration is used, the hermetic package for the cardiac wall motion sensor 168 must include electronics (not shown) to protect the cardiac wall motion sensor 168 from high voltage shocks that may be delivered by the patch electrode 160.

Referring now to FIG. 5, a further embodiment of an epicardial patch electrode in accordance with the principles of the present invention is described, in which a patch electrode 260, which includes all of the components of the patch electrode 60 of FIG. 3, further includes two cardiac wall motion sensors 268 and 269. In this embodiment, a carrier 262 includes a wire mesh 264 which may contact a region of the cardiac wall (not shown) through a plurality of windows 266 formed on one side of the carrier 262. The patch electrode 260 further includes the first cardiac wall motion sensor 268, which is located in a neck region 286 of the carrier 262, and is connected to two wires 270 and 272. A wire 274 connects the wire mesh 264 to the wire 270. The wires 270 and 272 extend through a branch 276 of an insulated cable 284 to a connector 280.

The second cardiac wall motion sensor 269 is connectable to an implantable cardiac stimulating device (not shown) by a set of two wires 271 and 273. The wire 271 branches from the wire mesh 264, or alternatively, from the wire 274 (the alternate branch is not shown). Even though both of the cardiac wall motion sensors 268 and 269 share an electrical connection with the wire mesh 264, a separate branch 278 of the cable 284 and an electrical connector 282 are preferred to support the wire 270. This is because of the ease of constructing a bifurcated connector over an in-line connector (not shown). However, it is recognized that a tripolar in-line connector (not shown) could be used. When a plurality of cardiac wall motion sensors are incorporated into the patch electrode 260, it is desirable, although not necessary, for each of the cardiac wall motion sensors to share an electrical connection with the wire mesh 264, to reduce the number of wires in the cable 284.

The patch electrode 260 incorporating the two cardiac wall motion sensors 268 and 269 offers several advantages over a single-sensor design. First, the cardiac wall motion sensors 268 and 269 are spaced apart with respect to one another so that propagation delays associated with cardiac contractions are sensed. The signal provided by each of the cardiac wall motion sensors 268 and 269 should therefore be nearly identical, but separated in time by the length of the propagation delay. Any differences in the signals can thus be attributed to body motion. Analyzing circuitry (not shown; described below) in the cardiac stimulating device can use the two signals to distinguish between cardiac wall motion and body movement. (As described below, the cardiac wall motion sensors of the present invention also include local electronics which substantially reduce low frequency body motion artifact in the cardiac wall motion sensor signal.) A second advantage is that a two-sensor system provides redundancy, so that each of the cardiac wall motion sensors 268 and 269 can be used to confirm the output of the other.

Referring now to FIG. 6, a three-sensor epicardial patch electrode in accordance with the principles of the present invention is described. In this embodiment, a patch electrode 360, which includes all of the components of the patch electrode 260 of FIG. 5, also includes three cardiac wall motion sensors 363, 368 and 369. The patch electrode 360 includes a carrier 362 having a wire mesh 364 disposed therein. The wire mesh 364 may contact a region of the cardiac wall (not shown) through a plurality of windows 366 formed on one side of the carrier 362.

The first cardiac wall motion sensor 368, which is located in a neck region 386 of the carrier 362, is connectable to an implantable cardiac stimulating device (not shown) by a set of two wires 370 and 372. A wire 374 connects the wire mesh 364 to the wire 370. The wires 370 and 372 extend through a branch 376 of an insulated cable 384 to a connector 380. The second cardiac wall motion sensor 369 is connectable to the implantable cardiac stimulating device by a set of two wires 371 and 373. The wire 371 branches from the wire mesh 364, or alternatively, from the wire 374 (the alternate branch is not shown). The wire 373 passes through a separate branch 378 of the insulated cable 384 and terminates at connector 382.

The third cardiac wall motion sensor 363 is connectable to the implantable cardiac stimulating device by a set of two wires 365 and 367. The wire 365 is preferably connected to the wire mesh 364 or alternatively, to the wire 374 (the alternate branch is not shown). The wire 367 extends through the branch 378 to connector 382, so that a bifurcated, bipolar connector can be used to terminate the insulated cable 384. In an alternative embodiment, a single quadrapolar in-line connector (not shown) may be used. It should be apparent to one skilled in the art that a second one-wire branch (not shown) and a second one-wire connector (not shown) could also be used to connect the wire 367 to the cardiac stimulating device.

The three-sensor embodiment of FIG. 6 offers the advantages of the two-sensor embodiment of FIG. 5, with greater reliability owing to the additional cardiac wall motion sensor. In addition, the output of the three cardiac wall motion sensors 363, 368 and 369, which are spaced appropriately apart within the patch electrode 360, may be used to compute a vector in the direction of cardiac wall motion. In any multi-sensor configuration, the location and size of the cardiac wall motion sensors may be varied as needed.

The patch electrodes 60, 160, 260 and 360 as described with respect to FIGS. 3–6 are all depicted as substantially rectangular; however, a patch electrode in accordance with the principles of the present invention may be constructed in a number of shapes to suit particular applications. For example, the patch electrodes 60, 160, 260 and 360 may be provided in shapes that conform to the shape of the left or right ventricular surfaces. Preferable shapes may include "butterfly," "rabbit-ear," "figure-eight" and triangular shapes, among others. The size and placement of the cardiac wall motion sensors may be modified as needed for a particular electrode shape.

Referring now to FIG. 7, a preferred embodiment of a myocardial active-fixation lead incorporating a cardiac wall motion sensor in accordance with the principles of the present invention is described. A myocardial active-fixation lead 90 includes a screw-in electrode 92 mounted at the distal end of the myocardial active-fixation lead 90 in an electrode mount 94. The electrode mount 94 is disposed within an electrically insulating, substantially inflexible carrier 96. The electrode 92, which is shown as a helical barb in FIG. 7, is intended to be screwed into myocardial tissue (not shown) when a cardiac stimulating device (not shown) is implanted. The electrode 92 typically serves as one pole in the delivery of therapeutic electrical stimulation, and is typically used in conjunction with a unipolar endocardial lead (not shown), or an epicardial patch electrode (not shown), which serves as the opposite pole.

In accordance with the invention, a cardiac wall motion sensor 468 is adhered to the electrode mount 94 with a biocompatible epoxy or silicone. The cardiac wall motion sensor 468 provides a signal indicative of motion of a region of the cardiac wall (not shown) to which the carrier 96 is attached. The cardiac wall motion sensor 468 is connectable to the implantable cardiac stimulating device by two wires 98 and 100, which are disposed within an insulated cable 102. Also disposed within the insulated cable 102 is a wire 104, which serves to connect the electrode 92 to the cardiac stimulating device.

The embodiment shown in FIG. 7 uses a bifurcated connector including two connectors 106 and 108 and two branches 110 and 112 (although a tripolar in-line terminal is also possible). Also, a two-wire configuration is also possible, in which the wire 104 is shared by the electrode 92 and the cardiac wall motion sensor 468, in a manner similar to that described for the epicardial patch electrode 160 of FIG. 4.

The shape of the electrode 92 may be selected to be any shape known to effectively penetrate the cardiac wall such that the electrode 92 is in contact with and secured to myocardial tissue. For example, the electrode 92 may alternatively be shaped as a spear.

Referring now to FIG. 8, a preferred embodiment of an endocardial lead incorporating a cardiac wall motion sensor in accordance with the principles of the present invention is described. In this embodiment, a lead body 114 of an endocardial lead 116 is preferably a flexible, multi-lumen catheter (as shown in detail in FIG. 11) made substantially from silicone rubber. As described in greater detail below, the lead body 114 serves as a carrier for delivering a cardiac wall motion sensor 568 to a region of the cardiac wall (not shown).

Extending from the distal end of the endocardial lead 116 is a helically-shaped tip electrode 118 which is connected to an electrode mount 120. Before the tip electrode 118 is secured to a region of the cardiac wall, the tip electrode 118 is substantially disposed within a screw housing 122. The tip electrode 118 is intended to be secured to myocardial tissue (not shown) of either the right atrium or the right ventricle.

A stylet 124 is used to facilitate securing the tip electrode 118 into myocardial tissue. The stylet 124 extends from the proximal end of the endocardial lead 116 to the tip electrode 118, and is disposed within a helically wound wire 126 within the lead body 114. The stylet 124 is typically removed from the endocardial lead 116 after the tip electrode 118 has been secured.

The endocardial lead 116 further includes a ring electrode 130. The ring electrode 130 is an electrically conductive cylinder, preferably made from a platinum/iridium alloy (with a typical platinum to iridium composition ratio of about $90/10$ or about $80/20$), that has an exposed external surface. The ring electrode 130 is connectable to an implantable cardiac stimulating device (not shown) by a wire 132 connected to a terminal 134 of a bifurcated, unipolar/tripolar in-line connector 136 (although other connectors may be used, such as a quadrapolar in-line connector). When the implantable cardiac stimulating device is used to provide pacing therapy, the tip electrode 118 typically serves as the cathode and the ring electrode 130 typically serves as the anode. In addition, cardiac electrical activity can be sensed between the tip electrode 118 and the ring electrode 130.

The lower portion of the ring electrode 130, as shown in FIG. 8, provides a passageway for the wire 126 and the stylet 124 disposed therein. The upper portion of the ring electrode 130 houses the cardiac wall motion sensor 568 (shown schematically in FIG. 8, and described in greater detail below). The cardiac wall motion sensor 568 provides a signal indicative of motion of a region of the cardiac wall (not shown) to which the endocardial lead 116 is affixed. A wire 138, which is connected to the cardiac wall motion sensor 568 by a feed through terminal 140 within a feed through 142, is used to electrically connect the cardiac wall motion sensor 568 to the implantable cardiac stimulating device. The cardiac wall motion sensor 568 is also connected to the ring electrode 130 by a wire 144 which provides a return line for the cardiac wall motion sensor 568. Such a configuration permits the endocardial lead 116 to be manufactured as a four-wire lead. But, as previously described, the cardiac wall motion sensor 568 should include electronics (not shown) to insulate the cardiac wall motion sensor 568 from stimulation pulses. Alternatively, a wire (not shown) may be provided to supply the cardiac wall motion sensor 568 with a dedicated return line, in which case, the endocardial lead 116 would contain five wires.

The endocardial lead 116 preferably further includes a shocking coil 146 for delivering high energy defibrillation shocks or low energy cardioversion shocks. The shocking coil 146 is electrically connectable to the implantable cardiac stimulating device by a wire 148 which is typically connected to a crimp tube (not shown) that is welded to a shocking coil termination ring 150. The wire 148 is connectable to the implantable cardiac stimulating device by a unipolar terminal 152 of the bifurcated connector 136. Typically, the shocking coil 146 is used in combination with an epicardial or subcutaneous patch electrode (not shown), or a second endocardial lead (not shown), or some combination, for delivering therapeutic shocks. Alternatively, the endocardial lead 116 may include a second shocking coil (not shown) positioned so that a defibrillation or cardioversion shock can be delivered between two coils on the same endocardial lead. Even further, an endocardial lead including two shocking coils, or two endocardial leads each including a single shocking coil, may be used in combination with an epicardial or subcutaneous patch electrode, to provide multiple current pathways and polarity selection for therapeutic shocks.

The wire 126 is used to electrically connect the tip electrode 118 to the implantable cardiac stimulating device. This is accomplished by removing the stylet 124 after the tip electrode 118 is secured, and inserting the bifurcated connector 136 of the endocardial lead 116 into a connector (not shown) in the implantable cardiac stimulation device, thereby electrically connecting the wires 126, 132, 138 and 148 to the pulse generating electronics (not shown) within the implantable cardiac stimulating device.

Figure 9:
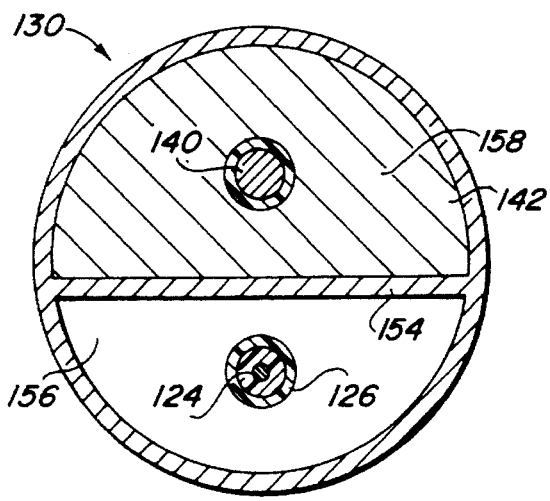
FIG. 9 is a cross-sectional view taken along line 9—9 of the endocardial lead shown in FIG. 8.
Figure 10:
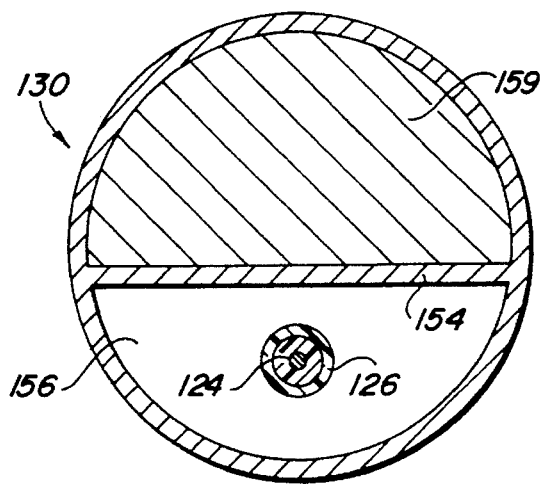
FIG. 10 is a cross-sectional view taken along line 10—10 of the endocardial lead shown in FIG. 8.

FIGS. 9 and 10 are cross-sectional views of the endocardial lead 116, depicting, respectively, the proximal and distal ends of the ring electrode 130. A wall 154, preferably made from a platinum/iridium alloy as previously described, divides the ring electrode 130 into two chambers that are preferably slightly unequal in size. The lower chamber 156, as shown in FIGS. 9 and 10, is open at both the proximal and distal ends of the ring electrode 130, in order to provide a passageway for the wire 126 and the stylet 124. The upper chamber 158 is enclosed by the feed through 142 at the proximal end and a plug 159 at the distal end. The feedthrough 142, described in greater detail below, provides passage for the feedthrough terminal 140 to the cardiac wall motion sensor 568. Preferably, the ring electrode 130, the wall 154, the feedthrough 142 and the plug 159 form a hermetically-sealed enclosure that serves as a housing for the cardiac wall motion sensor 568. Preferably, both the feedthrough 142 and the plug 159 are made substantially from a platinum/iridium alloy as previously described.

Figure 11:
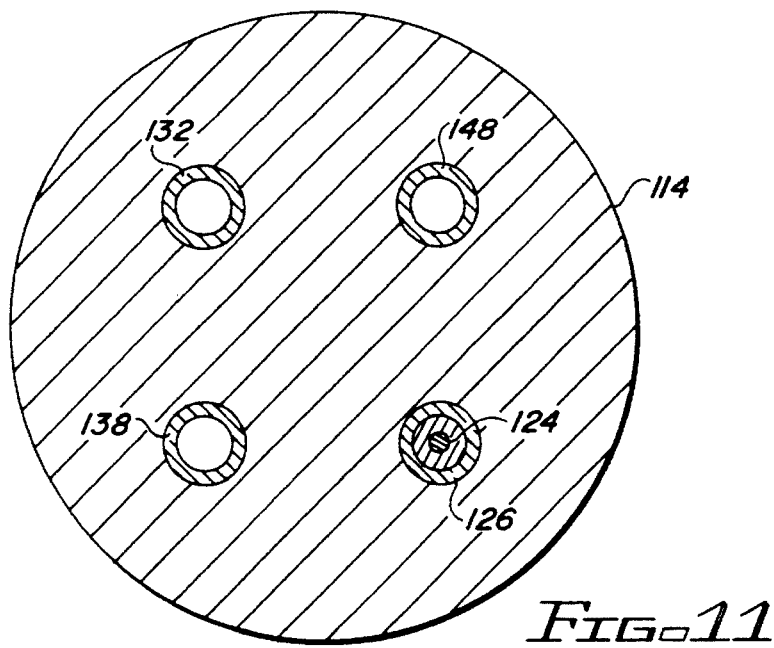
FIG. 11 is a cross-sectional view taken along line 11—11 of the endocardial lead shown in FIG. 8.

FIG. 11 is another cross-sectional view of the endocardial lead 116. This view shows the lead body 114 of the endocardial lead 116 as a four-lumen catheter, made substantially from silicone rubber. The four lumens contain the wires 126 (including the stylet 124 disposed therein), 132, 138 and 148. It should be apparent to one skilled in the art that the endocardial lead 116 may be constructed with additional lumens (or fewer lumens), depending on the number of wires that must be supported by the lead body 114.

The principles of the present invention as applied to the endocardial lead 116 of FIGS. 8–11 may be similarly applied to other endocardial leads known to be suitable for use with implantable cardiac stimulating devices. For example, the cardiac wall motion sensor 568 may be disposed within a unipolar endocardial pacing lead (not shown) or a dedicated cardioversion/defibrillation shocking lead (not shown). In such configurations, cardiac wall motion sensors would be disposed within separate housings (not shown) preferably made of a platinum/iridium alloy (as previously described) and located near the distal ends of the leads.

The means used to affix the endocardial lead 116 to endocardial tissue may also be modified to meet the needs of a particular application. For example, the screw housing 122 may include tines (not shown) to facilitate entrapment of the distal end of the endocardial lead 116 in fibrous endocardial tissue (not shown). In such a configuration, the tip electrode 118 need not serve as a fixation screw, and thus, may be manufactured in a blunt shape.

The endocardial lead used to deliver the cardiac wall motion sensor 568 to the cardiac wall may alternatively be a dedicated cardiac wall motion sensor lead (not shown) that does not include an electrode for delivering therapeutic electrical stimulation. This type of lead may be preferred when it is desirable to measure cardiac wall motion at a region remote from regions that are intended to receive electrical stimulation.

Figure 12:
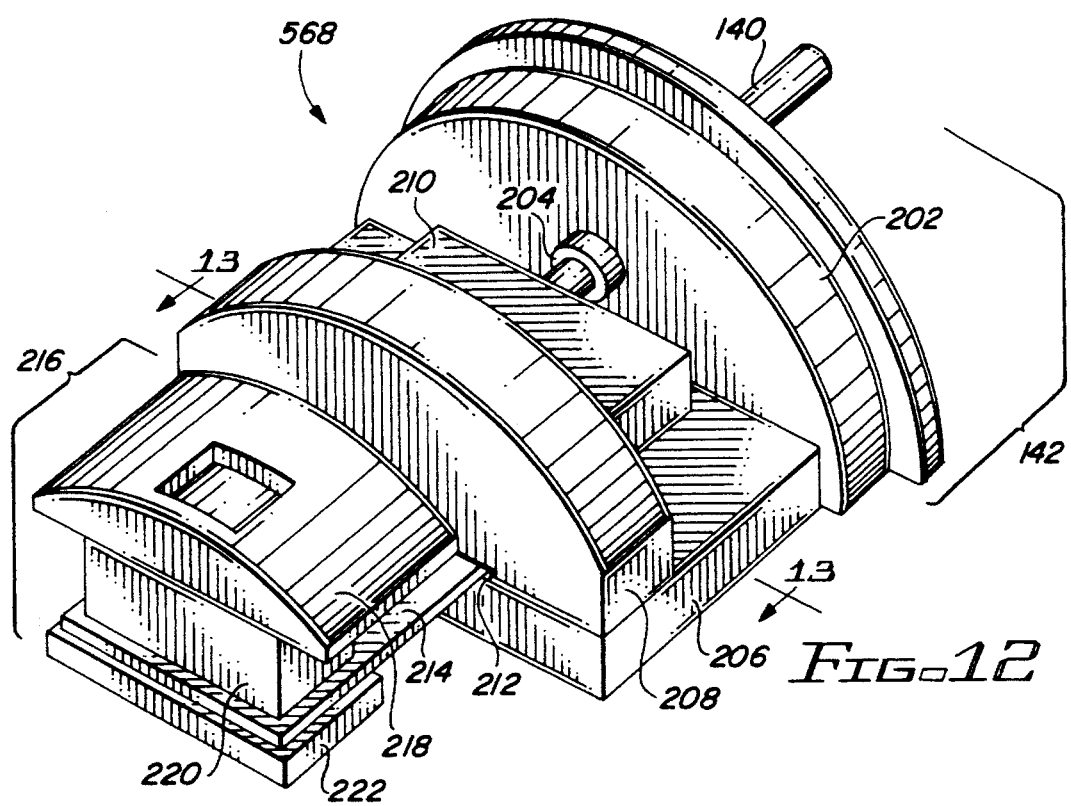
FIG. 12 is a perspective view of a preferred embodiment of a cardiac wall motion sensor in accordance with the principles of the present invention.

Referring now to FIG. 12, a preferred embodiment of a cardiac wall motion sensor is shown that is suitable for use as any of the cardiac wall motion sensors 68, 168, 268, 269, 363, 368, 369, 468 and 568 with the leads described with respect to FIGS. 3–8, as well as with other leads (not shown) that may be used in conjunction with an implantable cardiac stimulating device (not shown). For clarity, only the cardiac wall motion sensor 568 of FIG. 8 is referenced below.

This preferred embodiment of the cardiac wall motion sensor 568 is constructed as an accelerometer that is particularly well-suited for incorporation into an implantable cardiac stimulation device lead (not shown). The cardiac wall motion sensor is therefore capable of transducing accelerations of a region of the cardiac wall (not shown) to which a lead incorporating the cardiac wall motion sensor 568 is attached.

The accelerometer-based cardiac wall motion sensor 568 would typically be disposed within a housing such as the ring electrode 130 in the endocardial lead 116 of FIG. 8. Alternatively, the cardiac wall motion sensor 568 may be disposed within a separate, hermetically sealed housing (not shown), preferably made from a platinum/iridium alloy (as previously described), so that it may be mounted in an epicardial patch electrode (as shown in FIGS. 3–6), a myocardial active-fixation lead (as shown in FIG. 7), an endocardial lead that does not have a ring electrode (not shown), or some other lead that is suitable for use with an implantable cardiac stimulating device (not shown).

The cardiac wall motion sensor 568 includes a feedthrough 142 that hermetically seals the cardiac wall motion sensor 568 within the sensor housing (not shown), while permitting the feedthrough terminal 140 to pass therethrough. The feedthrough terminal 140 allows for connection to the wire 138 (shown in FIG. 8). Attachment is typically made by inserting the feedthrough terminal 140 into the coaxially wound wire 138 and securing the wire 138 by crimping, laser welding, or other conventional methods. The feedthrough 142 includes a feedthrough body 202, which is used to hermetically seal one end of the sensor housing. When the cardiac wall motion sensor 568 is used with an epicardial or myocardial lead (not shown), the feedthrough 142 may be an integral part of the sensor housing. The feedthrough body 202 is preferably made from the same material as the sensor housing, preferably, a platinum/iridium alloy.

The feedthrough 142 further includes an insulating ring 204, which is preferably made from an electrically insulating material such as glass or ceramic. The insulating ring 204 insulates the feedthrough terminal 140 from the sensor housing. The feedthrough terminal 140 delivers an electrical signal indicative of cardiac wall motion, and more particularly, indicative of cardiac wall accelerations, from the accelerometer-based cardiac wall motion sensor 568 to the wire 138 (shown in FIG. 8), which transmits the signal to the implantable cardiac stimulating device. The feedthrough 142 may further include an additional feedthrough terminal (not shown) which would be connected to a separate ground line for local electronics 210, as described below.

A substrate 206, which is affixed to the interior of the feedthrough 142 (or alternatively, to the wall 154 in the ring electrode 130 shown in FIGS. 9 and 10) is made from a non-conductive material such as plastic or ceramic. The substrate 206 serves as a base member upon which a mount 208 is affixed, and upon which the local electronics 210 are mounted. The substrate 206 and the mount 208 form a slot 212, which is used as an anchor for one end of a cantilever beam 214, and also provides structural support to the sensor housing.

Adhered to the distal end of the cantilever beam 214 is an offset mass assembly 216. The offset mass assembly 216 may be constructed in a variety of ways. In a preferred embodiment, the offset mass assembly 216 includes a mass 218 made from a dense, nonferrous material, such as tungsten, platinum, brass or bronze, supported on the cantilever beam 214 by a mass mount 220 and a mass backing 222. The mass mount 220 and the mass backing 222 offset the mass 218 from the planar surface of the cantilever beam 214, so that the cardiac wall motion sensor 568 is responsive to accelerations which occur in directions along the axis of the lead body 114 (shown in FIG. 8) and perpendicular to the planar surface of the cantilever beam 214. The mass mount 220 and the mass backing 222 may be made from a light plastic material, such as acrylonitrile butadiene styrene (ABS), available from GE Plastics Company of Pittsfield, Mass.

Although it is possible to use a mass symmetrically disposed on the free end of the cantilever beam 214, the offset mass assembly 216 is preferred because it enables the cardiac wall motion sensor 568 to provide a signal indicative of cardiac wall motion in directions along at least two perpendicular axes. If a symmetrical mass is used, the cardiac wall motion sensor 568 becomes uniaxial, and care must be taken to ensure that the lead used to deliver the cardiac wall motion sensor 568 is attached to a region of the cardiac wall in such a way as to be most sensitive to accelerations in the directions of significant cardiac wall motion.

The cantilever beam 214 incorporates a material that has an electrical characteristic that varies measurably in response to conformational changes in the beam 214. In a preferred embodiment, the material is a piezoelectric material, such as polyvinylidene fluoride (commonly known by the trademark KYNAR, owned by ATOCHEM North America). When the cantilever beam 214 incorporates a piezoelectric material, an electrical potential is generated between the surfaces of the beam 214 when the beam 214 experiences a mechanical stress or strain.

When a piezoelectric material is used, the cantilever beam 214 may be constructed in several ways. In a preferred embodiment, the cantilever beam 214 has a piezoelectric film (not shown) adhered to each surface of a metallic substrate (not shown), such as a titanium substrate, to form a piezoelectric bimorph. The cantilever beam 214 may alternatively be constructed with a piezoelectric film on only one surface of a metallic substrate, to form a piezoelectric monomorph. Also, the cantilever beam 214 may be constructed as a piezoelectric bimorph in which the piezoelectric films are adhered to one another and not separated by a substrate.

Figure 13:
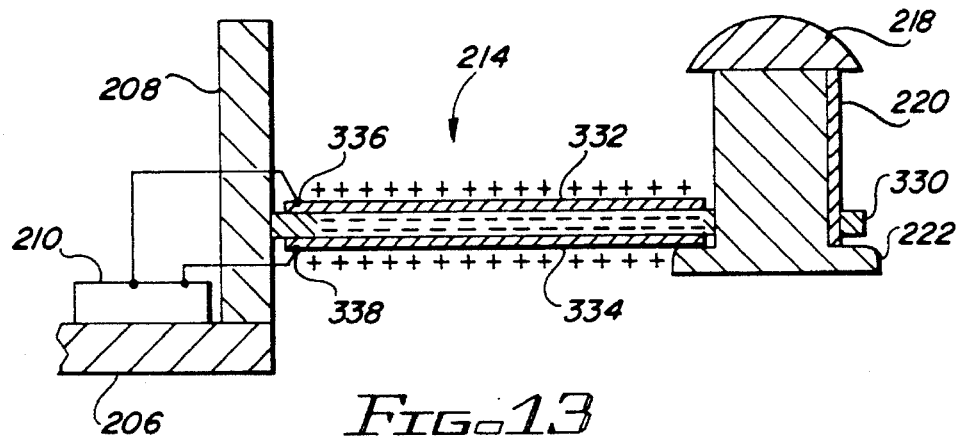
FIG. 13 is a cross-sectional view taken along line 13—13 of the cardiac wall motion sensor shown in FIG. 12, showing a cantilever beam of the cardiac wall motion sensor in a resting state.
Figure 14:
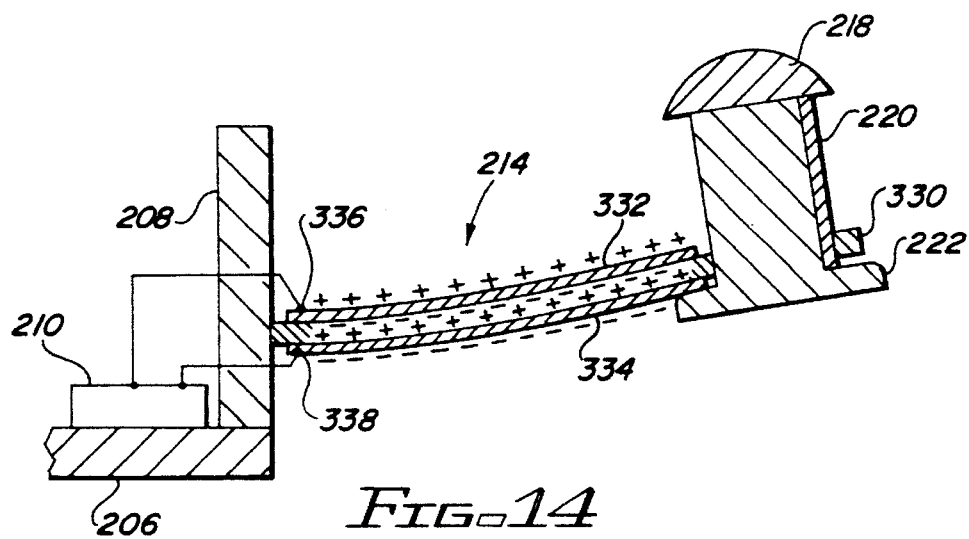
FIG. 14 is a cross-sectional view taken along line 13—13 of the cardiac wall motion sensor shown in FIG. 12, showing an upward deflection of a cantilever beam of the cardiac wall motion sensor in accordance with the principles of the present invention.
Figure 15:
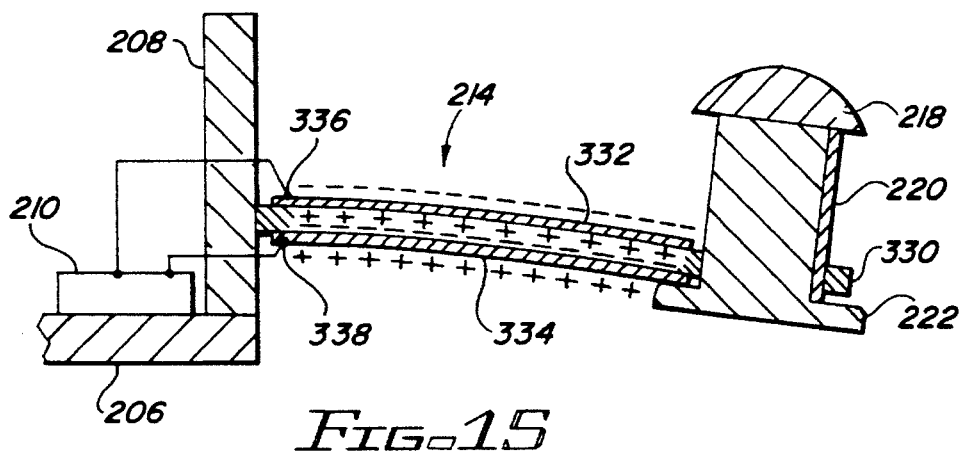
FIG. 15 is a cross-sectional view taken along line 13—13 of the cardiac wall motion sensor shown in FIG. 12, showing a downward deflection of a cantilever beam of the cardiac wall motion sensor in accordance with the principles of the present invention.

FIGS. 13, 14 and 15 show a cross-sectional view of the preferred embodiment of the cantilever beam 214. FIG. 13 corresponds to the resting state of the cantilever beam 214 (no motion), while FIGS. 14 and 15 correspond to upward and downward deflections of the cantilever beam, respectively. The cantilever beam 214 includes a metallic substrate 330, which is preferably a titanium substrate, having two piezoelectric films 332 and 334 adhered to the top and bottom surfaces of the metallic substrate 330. The piezoelectric films 332 and 334 are polarized such that one surface of each film has a positive charge and the other surface of each film has a negative charge. As shown in FIG. 13, the piezoelectric films 332 and 334 are adhered to the metallic substrate 330 such that the negatively charged surface of each of the piezoelectric films 332 and 334 makes contact with the metallic substrate 330. The piezoelectric films 332 and 334 are constructed with contacts 336 and 338, respectively, which are used to connect the piezoelectric films 332 and 334 to the local electronics 210. The contacts 336 and 338 are formed on the piezoelectric films 332 and 334 during a metallization process.

FIG. 14 shows the change in polarization of the piezoelectric film 334 during an upward deflection of the cantilever beam 214, caused by an acceleration experienced by the cardiac wall motion sensor 568. As the piezoelectric film 334 is bent upward, the polarization of the piezoelectric film 334 inverts and a negative charge is seen at the contact 338. The piezoelectric film 332 retains a positive charge on its outer surface, which is seen at the contact 336. The positive charge at the contact 336 and the negative charge at the contact 338 create an overall positive potential which is seen by the local electronics 210. The magnitude of the positive potential varies in accordance with the magnitude of the deflection of the cantilever beam 214.

Conversely, FIG. 15 shows the change in polarization of the piezoelectric film 332 during a downward deflection of the cantilever beam 214. As the piezoelectric film 332 is bent downward, the polarization of the piezoelectric film 332 inverts and a negative charge is seen at the contact 336. The piezoelectric film 334 retains a positive charge on its outer surface, which is seen at the contact 338. The positive charge at the contact 338 and the negative charge at the contact 336 create an overall negative potential which is seen by the local electronics 210. In this manner, the local electronics 210 measures both the magnitude and sign of the potentials that appear across the cantilever beam 214 to provide signals indicative of cardiac wall motion, and more particularly, accelerations of a region of the cardiac wall.

In an alternative embodiment similar to that described with respect to FIG. 12, a piezoresistive material may be used instead of a piezoelectric material. A piezoresistive material undergoes a change in resistance when the material is subjected to a mechanical stress or strain. When a piezoresistive material is used, a cantilever beam (not shown) similar to the cantilever beam 214 of FIG. 12 includes a substrate (not shown), preferably made from titanium, upon which the piezoresistive material (not shown) is deposited. Preferably, two piezoresistive deposits (not shown) are provided on the cantilever beam, one on each side. The cantilever beam having two piezoresistive deposits provides for temperature compensation, which is desirable because the piezoresistive effect of many such materials varies greatly with fluctuations in temperature.

In another alternative embodiment, implantable cardiac stimulation leads may be constructed to include other types of transducers, such as strain gauges (not shown), that are capable of providing signals indicative of cardiac wall motion to the implantable cardiac stimulating device.

Figure 16:
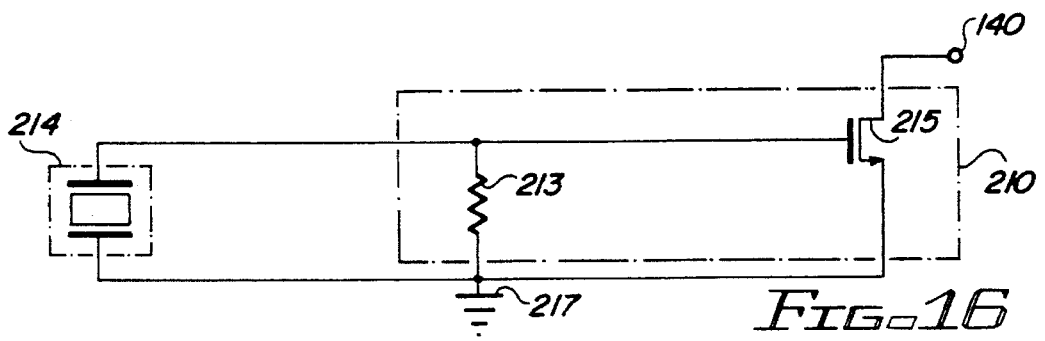
FIG. 16 is a schematic diagram of a preferred embodiment of local electronics for the cardiac wall motion sensor shown in FIG. 12 in accordance with the principles of the present invention.

Referring now to FIG. 16, the local electronics 210 for the preferred embodiment of the cardiac wall motion sensor 568 that includes a piezoelectric material are described. In the preferred embodiment, one surface of the cantilever beam 214 is connected to one end of a resistor 213 and to the gate of a field effect transistor (FET) 215 of the local electronics 210. The resistor 213, which typically has a very high value of resistance, may be about 10 gigaohms. The opposite surface at the cantilever beam 214 is connected to a ground node 217, which in the preferred embodiment is the ring electrode 130 (shown in FIG. 8). The other end of resistor 213 and the source of the FET 215 are also connected to the ground node 217. Alternatively, the resistor 213 and the source of the FET 215 may be connected through an additional feedthrough terminal (not shown) to an isolated ground line (not shown). The output signal of the local electronics is obtained from the drain of the FET 215, which is connected to the feedthrough terminal 140 (shown in FIG. 12).

The local electronics 210, which are suitable for the preferred embodiment of the cardiac wall motion sensor 568 of FIG. 12 that incorporates a piezoelectric material, provide a buffer between a high impedance source (the piezoelectric material of cardiac wall motion sensor 568) and a low impedance load (an implantable cardiac stimulating device). The local electronics 210 also provide signal processing functions to select or reject components of body movement or cardiac accelerations.

If a cardiac wall motion sensor (not shown) is designed so as to incorporate a piezoresistive material, local electronics (not shown) provide electrical connections (not shown) to each piezoresistive deposit (not shown) on the cantilever beam (not shown). The local electronics for a piezoresistive embodiment also provide bridge circuitry (not shown) for measuring variations in the resistances of the piezoresistive deposits. Preferably, a two-active arm bridge is used in conjunction with two piezoresistive deposits on the cantilever beam, so as to compensate for resistance variations associated with fluctuations in temperature. The local electronics for a piezoresistive embodiment may also include a high-pass filter (not shown) for filtering out body motion artifact.

Referring again to FIG. 12, the cardiac wall motion sensor 568 constructed with a single cantilever beam 214 and the offset mass assembly 216 is capable of transducing cardiac wall accelerations in directions along two perpendicular axes. Specifically, accelerations in directions along the axis perpendicular to the planar surface of the cantilever beam 214 upon which the offset mass assembly 216 is mounted, and in directions along the axis extending from the fixed end to the free end of the beam (the lead body axis), will result in mechanical stresses and strains being applied to the piezoelectric or piezoresistive material. In the case of a piezoelectric material, the mechanical stresses and strains induce measurable electrical potentials between the surfaces of the material, which potentials are indicative of the mechanical activity of a region of the cardiac wall to which a lead incorporating the cardiac wall motion sensor 568 is attached. Preferably, the induced potentials are locally processed by the local electronics 210, and made available to the cardiac stimulating device via the feedthrough terminal 140.

When a piezoresistive material is used, the mechanical stresses and strains result in measurable changes in the resistance of the material, which changes in resistance are indicative of the mechanical activity of a region of the cardiac wall to which a lead incorporating the cardiac wall motion sensor (not shown) is attached. Preferably, the resistance variations are measured using bridge circuitry (not shown) in local electronics (not shown) provided for the piezoresistive cardiac wall motion sensor.

As previously described, the cardiac wall motion sensor 568, as depicted in FIG. 12, provides multi-axis sensitively to cardiac wall motion. However, in this configuration, there is little sensitivity to cardiac wall motion in directions along the third axis, which in this embodiment, is perpendicular to the narrow edges of the cantilever beam 214. Thus, when the cardiac wall motion sensor 568 is disposed within an endocardial lead (e.g., the endocardial lead 116 shown in FIG. 8), any rotation of the lead may result in reduced output in response to cardiac wall motion in certain directions.

Figure 17:
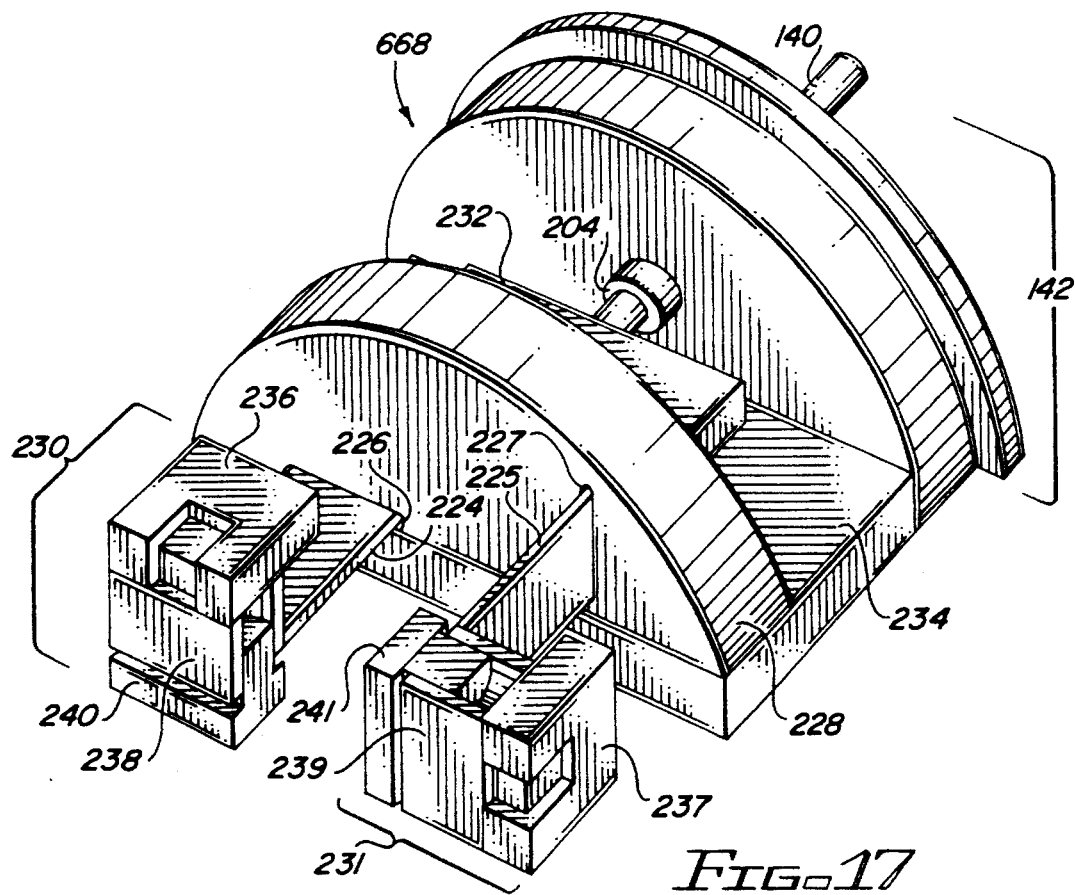
FIG. 17 is a perspective view of another preferred embodiment of a cardiac wall motion sensor in accordance with the principles of the present invention.

Referring now to FIG. 17, an alternative embodiment of a cardiac wall motion sensor 668 is described that provides triple-axis sensitivity. The cardiac wall motion sensor 668 is also suitable for use with the leads described with respect to FIGS. 3–11, as well as other leads that may be used in conjunction with an implantable cardiac stimulating device (not shown). In this embodiment, two cantilever beams 224 and 225 are mounted orthogonally to one another in two slots 226 and 227, respectively, of a mount 228. Two offset mass assemblies 230 and 231 are individually mounted to each of the cantilever beams 224 and 225, respectively. Alternatively, symmetrical masses (not shown) may be mounted to each of the cantilever beams 224 and 225 to provide two orthogonal axes of sensitivity in the radial direction. In the offset configuration, the cantilever beams 224 and 225 are responsive to accelerations along the axes perpendicular to the surfaces upon which their respective offset mass assemblies 230 and 231 are mounted, and along the lead body axis.

The orthogonal orientation of the cantilever beams 224 and 225 may enable the cardiac wall motion sensor 668 to provide substantial output despite an occurrence of lead rotation. As the cardiac wall motion sensor 668 rotates, the output provided by one of the cantilever beams 224 or 225 increases, as the output provided by the other decreases. In addition, the orthogonally oriented cantilever beams 224 and 225 can provide a redundant axis of sensitivity. The cardiac wall motion sensor 668 may be secured to a region of the cardiac wall (not shown) in a position such that the magnitude of cardiac tissue accelerations in directions along the redundant axis is substantial. Thus, if one of the cantilever beams 224 or 225 fails to provide a signal, for example, in the event of a faulty electrical connection, the other cantilever beam may still provide a signal. When the cantilever beams 224 and 225 are incorporated into the cardiac wall motion sensor 668, local electronics 232 may include circuitry to provide one signal representing accelerations measured by both beams.

Manufacturing of the cardiac wall motion sensor 668 is accomplished in a manner similar to that of the cardiac wall motion sensor 558 of FIG. 12. A substrate 234 is affixed to the interior of the feedthrough 142, or alternatively, to the wall 148 in ring electrode 130 (shown in FIGS. 9 and 10) to provide a base upon which the mount 228 and the local electronics 232 are mounted. The offset mass assemblies 230 and 231 include masses 236 and 237, respectively, supported on the cantilever beams 224 and 225, respectively, by two mass mounts 238 and 239, respectively, and two mass backings 240 and 241, respectively.

Referring now to FIG. 18, an implantable cardiac stimulating device for delivering therapeutic electrical stimulation in response to cardiac arrhythmias detected using leads incorporating cardiac wall motion sensors in accordance with the principles of the present invention is described. The implantable cardiac stimulating device described with respect to FIG. 18 is capable of providing "tiered therapy" in response to cardiac arrhythmias which are diagnosed as pathological, and is also capable of providing bradycardia pacing support. The principles as described herein may also be applied to devices that only provide selected therapies, for example, dedicated pacemakers or dedicated defibrillators.

An implantable cardiac stimulating device 242 includes a housing 244, which protects the components contained therein from bodily fluids. The implantable cardiac stimulating device 242 receives input (depicted schematically as a single input in FIG. 18) from at least one cardiac wall motion sensor (not shown), which may be delivered to a region of the cardiac wall (not shown) using the leads described above with respect to FIGS. 3–8, among others. Preferably, the implantable cardiac stimulating device 242 receives input from a plurality of cardiac wall motion sensors (not shown) that transduce cardiac wall motion at a plurality of regions of the cardiac wall. In this preferred embodiment, the cardiac wall motion sensors are accelerometer-based, and the signals thus provided are indicative of accelerations of the cardiac wall.

The cardiac wall motion sensor signal is received by an amplifier 246 (or a plurality of such amplifiers if a plurality of cardiac wall motion sensors are used). The amplified signal (or signals) is provided to an accelerometer signal analyzer 248. The accelerometer signal analyzer 248 analyzes each amplified signal in order to measure cardiac wall motion. More particularly, the accelerometer signal analyzer 248 is capable of detecting an occurrence of an abnormal cardiac rhythm, identifying the type of cardiac arrhythmia (e.g., tachycardia or ventricular fibrillation) after an occurrence is detected, and, when a plurality of cardiac wall motion sensors are used, determining the location of the arrythmia if the arrhythmia is isolated.

The accelerometer signal analyzer 248 may also use the amplified signals to determine intrinsic heart rate. Furthermore, when a plurality of cardiac wall motion sensors are used within a single lead, for example, the epicardial patch electrodes 260 and 360 described with respect to FIGS. 5 and 6, the accelerometer signal analyzer 248 may measure propagation delays associated with cardiac contractions, and use the measured propagation delays to filter out body motion artifact.

The implantable cardiac stimulating device 242 may further receive input indicative of cardiac electrical activity from sensing electrodes (depicted schematically as a single line in FIG. 18). Cardiac electrical activity may be sensed using electrodes disposed within leads as described with respect to FIGS. 3–8. For example, cardiac electrical activity may be sensed between the ring electrode 130 and the tip electrode 118 of the endocardial lead 116 described with respect to FIG. 8. Furthermore, the implantable cardiac stimulating device 242 may be constructed to receive a plurality of signals indicative of cardiac electrical activity. Thus, the implantable cardiac stimulating device 242 is capable of receiving signals indicative of cardiac mechanical activity and cardiac electrical activity.

A signal indicative of cardiac electrical activity is received by an amplifier 250 (or a plurality of such amplifiers if a plurality of signals are received). The amplified signal (or signals) is supplied to an electrical activity signal analyzer 252, which can analyze each signal in order to measure cardiac electrical activity. The electrical activity signal analyzer 252 may be a conventional R-wave detector that measures intrinsic heart rate. Similar to the accelerometer signal analyzer 248, the electrical activity signal analyzer 252 may be capable of detecting the onset of various cardiac arrhythmias, and identifying the type and location of detected cardiac arrhythmias.

In a preferred embodiment, the implantable cardiac stimulating device 242 receives a plurality of signals indicative of cardiac electrical activity. However, a device that receives only one signal indicative of cardiac electrical activity may also be constructed. Furthermore, an implantable cardiac stimulating device may be constructed that does not utilize signals indicative of cardiac electrical activity. In such a device (not shown), cardiac activity is measured exclusively by analyzing signals indicative of cardiac tissue accelerations.

The accelerometer signal analyzer 248 and the electrical activity signal analyzer 252 each supply a signal to a control logic circuit 254. The signals from the respective analyzers 248 and 252 may provide encoded information identifying the type, severity and location of detected cardiac arrhythmias, as well as information relating to intrinsic heart rate.

The control logic 254 may be configured by a physician using an external telemetry unit 256 via a telemetry stage 258 to operate in one of several modes. The control logic 254 may be configured to respond to signals from either the accelerometer signal analyzer 248 or the electrical activity signal analyzer 252 exclusively. Alternatively, the control logic 254 may be configured to respond primarily to either the accelerometer signal analyzer 248 or the electrical activity signal analyzer 252, and to use the information provided by the analyzer not designated as the primary source of information as a secondary source of information. The analyzer selected as the secondary source of information could be used to confirm the presence of cardiac arrhythmias detected by the primary source of information. Furthermore, the extent to which a particular type of signal is used may be varied for each type of electrical stimulation therapy. For example, the accelerometer signal analyzer 248 may be designated as the primary source of information used to identify tachycardias and ventricular fibrillation, whereas the electrical activity signal analyzer 252 may be the primary source of information for use in providing bradycardia pacing support.

Although the telemetry stage 258 is depicted in FIG. 18 as being directly connected only to the control logic 254, it may communicate with several or all of the components within the implantable cardiac stimulating device 242. For example, the telemetry stage 258 may transmit signals received by either the accelerometer signal analyzer 248 or the electrical activity signal analyzer 252, or both, to the external telemetry unit 256.

In the absence of cardiac arrhythmias requiring antitachycardia, cardioversion or defibrillation therapy, the control logic 254 may use information provided by either the accelerometer signal analyzer 248 alone, the electrical activity signal analyzer 252 alone, or some combination of signals received therefrom, depending on how the control logic 254 is configured, to enable a bradycardia pacing control stage 290, which controls the delivery of bradycardia pacing pulses from a pacing pulse output stage 292. Bradycardia pacing support may be provided using any of the known pacing modes, including any of the dual chamber pacing modes, such as DDD pacing. The use of cardiac wall motion sensor signals for bradycardia pacing is advantageous as compared to the more common method of relying substantially upon monitoring the electrical activity of the heart because the accelerometer will continue to accurately sense cardiac activity even during the after-potential period.

The control logic 254 may respond to potentially malignant cardiac arrhythmias detected by the accelerometer signal analyzer 248 alone, the electrical activity signal analyzer 252 alone, or some combination of signals received therefrom, depending on the selected configuration. When the control logic 254 is supplied with information indicative of tachycardia, it may enable an antitachycardia pacing control stage 294, which controls the delivery of antitachycardia pacing pulses from the pacing pulse output stage 292. The sequence of pacing pulses used may be any of the antitachycardia pacing sequences known for terminating the detected tachycardia. Alternatively, and particularly if the tachycardia is deemed severe, the control logic 254 may enable a cardioversion/defibrillation control stage 296, which controls the delivery of low energy cardioversion shocks from a high energy pulse generator 298. If one or both of the signal analyzers 248 and 252, depending on the selected configuration, detects the onset of ventricular fibrillation, the control logic 254 enables the cardioversion/ defibrillation control stage 296, which also controls the delivery of high energy defibrillation shocks from the high energy pulse generator 298.

Electrical stimulation therapy provided by the implantable cardiac stimulating device 242 may be delivered to cardiac tissue (not shown) using the leads described with respect to FIGS. 3–8, among others. Typically, pacing pulses generated by the pacing pulse output stage 292 are delivered to cardiac tissue via the same electrodes that are used to sense cardiac electrical activity. For example, in the endocardial lead 116 described with respect to FIG. 8, pacing pulses are delivered between the tip electrode 118 and the ring electrode 130, and cardiac electrical activity is sensed between the same two electrodes 118 and 130 when pacing pulses are not being delivered.

Cardioversion and defibrillation shocks are delivered using a plurality of high energy shocking electrodes. The high energy shocking electrodes may be delivered to cardiac tissue using the leads described with respect to FIGS. 3–8. For example, the endocardial lead 116 described with respect to FIG. 8 may be constructed with two high energy shocking coils (one of which is not shown), one of which serves as the anode, and the other of which serves as the cathode. In addition, any of the patch electrodes 60, 160, 260 and 360 may be used to deliver cardioversion and defibrillation shocks. Preferably, more than two high energy shocking electrodes are used, in order to provide greater flexibility in delivering cardioversion and defibrillation shocks.

Figure 19:
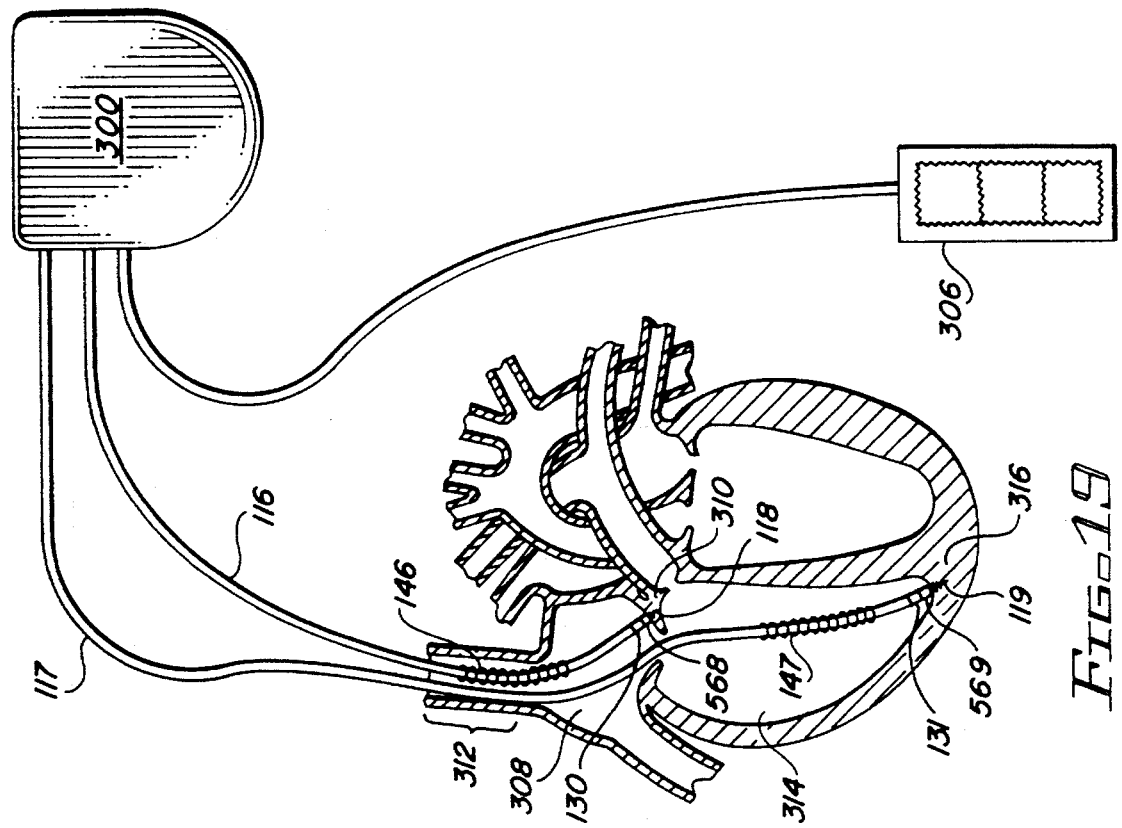
FIG. 19 illustrates a preferred configuration of an implantable system for delivering therapeutic electrical stimulation to cardiac tissue that uses two bipolar endocardial leads incorporating cardiac wall motion sensors in accordance with the principles of the present invention and a subcutaneous patch electrode.

An implantable cardiac stimulating device may be used in combination with a variety of lead configurations, in order to meet the needs of a particular application. In a preferred configuration shown in FIG. 19, an implantable cardiac stimulating device 300 is used with a subcutaneous patch electrode 306, and two endocardial leads 116 and 117 which include cardiac wall motion sensors 568 and 569, respectively, within ring electrodes 130 and 131, respectively, as shown in FIG. 8. The first endocardial lead 116 is transvenously delivered to a right atrium 308 and secured to endocardial tissue 310 therein. The first endocardial lead 116 is positioned so that a ring electrode 130 and a tip electrode 118 are in electrical contact with a region of the endocardial tissue 310 in the right atrium 308, and a high energy shocking coil 146 is contained substantially within a superior vena cava 312. The other endocardial lead 117 is transvenously delivered to a right ventricle 314 and is secured so that a ring electrode 131 and a tip electrode 119 are in electrical contact with a region of endocardial tissue 316 in the right ventricle 314, and a high energy shocking coil 147 is contained within the right ventricle 314. The subcutaneous patch electrode 306, which may not incorporate a cardiac wall motion sensor, is subcutaneously implanted beneath skin on the chest of the patient.

In this configuration, the implantable cardiac stimulating device 300 receives information indicative of cardiac wall motion from the two cardiac wall motion sensors 568 and 569, and also receives input indicative of cardiac electrical activity from two sets of ring electrodes 130 and 131 and tip electrodes 118 and 119. More particularly, the implantable cardiac stimulating device 300 receives signals indicative of cardiac mechanical activity and cardiac electrical activity of both the right atrium 308 and the right ventricle 314.

The implantable cardiac stimulating device 300, thus configured, may provide bradycardia pacing pulses between the ring electrodes 130 and 131 and the corresponding tip electrodes 118 and 119, in each of the endocardial leads 116 and 117. In this configuration, pacing pulses are delivered by the same set of physical wires (not shown) that are used to sense cardiac electrical activity. Cardioversion/ defibrillation pulses are provided by the two high energy shocking coils 146 and 147 and the subcutaneous patch 306.

This type of multiple-input, multiple-output configuration offers several advantages with respect to both bradycardia pacing support and tiered therapy. With respect to bradycardia pacing, this configuration permits dual-chamber sensing of cardiac mechanical activity and cardiac electrical activity. Cardiac mechanical activity, as transduced by the cardiac wall motion sensors 568 and 569 in the right atrium 308 and the right ventricle 314, may be used by the control logic 254 and the bradycardia pacing control stage 290 (as shown in FIG. 18) to control the delivery of pacing pulses to either the right atrium 308, the right ventricle 314, or some combination of the two. Alternatively, measured cardiac electrical activity may be used as the primary or secondary source of information for controlling the delivery of bradycardia pacing pulses.

With respect to tiered therapy, the use of a plurality of cardiac wall motion sensors serves to more precisely isolate the location of the arrhythmia. In response to an arrhythmia detected at a particular location, the control logic 254 and the cardioversion/defibrillation control stage 296 (as shown in FIG. 18) can control the delivery of therapeutic electrical stimulation in at least two ways. Specifically, the number of high energy shocking electrodes that are activated, and the polarities of the activated electrodes, may be controlled by the control logic 254 and the cardioversion/defibrillation control stage 296. In this manner, the number of current pathways through the cardiac tissue 316, and the direction of current flow with respect to each current pathway, may be configured so as to provide the most effective therapy for a particular arrhythmia.

Figure 20:
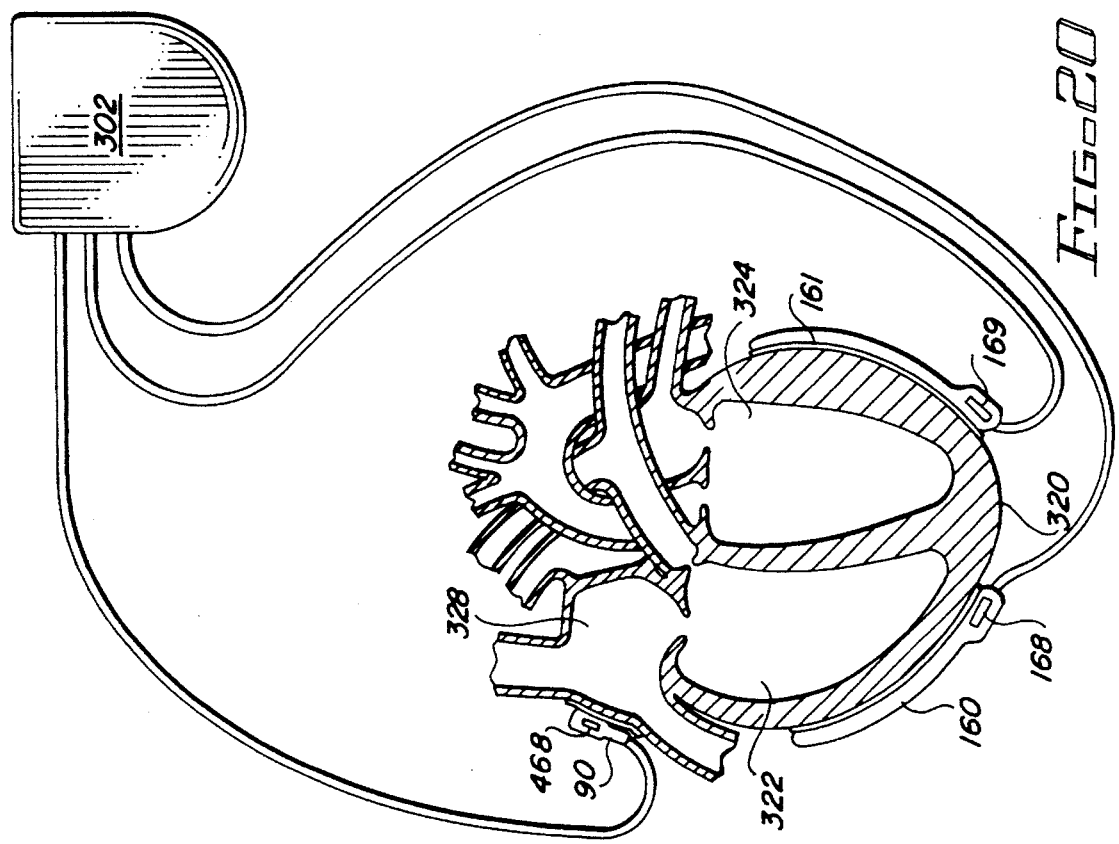
FIG. 20 is another preferred configuration of an implantable system for delivering therapeutic electrical stimulation to cardiac tissue that uses two patch electrodes and a myocardial active-fixation lead, each incorporating a cardiac wall motion sensor in accordance with the principles of the present invention.

In another preferred configuration shown in FIG. 20, an implantable cardiac stimulating device 302 is used with two epicardial patch electrodes 160 and 161 incorporating cardiac wall motion sensors 168 and 169, respectively, (as described with respect to FIGS. 3–6). Preferably, the patch electrode 160 is sutured to a region of the epicardium 320 in the vicinity of a right ventricle 322, and the patch electrode 161 is sutured to a region of the epicardium 320 in the vicinity of a left ventricle 324. In addition, a myocardial active-fixation lead 90 including a cardiac wall motion sensor 468 (as described with respect to FIG. 7) may also be used, and is affixed to the epicardium 320 in the region of a right atrium 328. This configuration offers the advantages of cardiac mechanical activity sensing at a plurality of cardiac tissue regions (using sensors 468, 168, 169) and controlled delivery of electrical stimulation therapy to selected regions of cardiac tissue. A further advantage of a configuration that employs an epicardial patch electrode incorporating a cardiac wall motion sensor is that activity of the left ventricle may be sensed.

Thus, implantable leads incorporating cardiac wall motion sensors are provided. One skilled in the art will appreciate that the present invention can be practiced by other than the described embodiments, which are presented for purposes of illustration and not of limitation, and the present invention is limited only by the claims which follow.

What is claimed is:

1. An implantable system for detecting and discriminating among cardiac arrhythmias and for providing therapeutic electrical stimulation to cardiac tissue in response to detected cardiac arrhythmias, said implantable system comprising:

an implantable lead including electrode means for delivering therapeutic electrical stimulation pulses to said cardiac tissue and for transmitting a signal indicative of cardiac electrical activity to said implantable system, said implantable lead further including a cardiac wall acceleration sensor for providing a signal indicative of cardiac wall accelerations;

acceleration signal analyzing means for receiving said signal indicative of cardiac wall acceleration and for using said signal to detect and discriminate among cardiac arrhythmias; and pulse generating means for generating said therapeutic electrical stimulation pulses for delivery to said cardiac tissue by said electrode means in response to cardiac arrhythmias detected by said cardiac wall acceleration signal analyzing means.

2. The implantable system of claim 1, further comprising:

electrical activity analyzing means for receiving said signal indicative of cardiac electrical activity transmitted by said electrode means and for using said signal indicative of cardiac electrical activity to detect and discriminate among cardiac arrhythmias; and control means for enabling said pulse generating means to respond primarily to one of said acceleration signal analyzing means and said electrical activity analyzing means.

3. The implantable system of claim 1, wherein said cardiac wall acceleration sensor comprises an accelerometer.

4. The implantable system of claim 3, wherein said accelerometer includes a central axis, said accelerometer being responsive to cardiac wall accelerations along said central axis and to accelerations perpendicular to said central axis.

5. The implantable system of claim 3, wherein said implantable lead comprises a plurality of conductors for connecting said accelerometer to said acceleration signal analyzing means and for connecting said electrode means to said pulse generating means.

6. The implantable system of claim 3, wherein said implantable lead comprises a flexible patch, and said accelerometer and said electrode means are disposed within said patch.

7. The implantable system of claim 3, wherein:

said implantable lead comprises a substantially inflexible myocardial electrode mount, said electrode mount having an active-fixation helix protruding therefrom; and said accelerometer is secured to said electrode mount.

8. The implantable system of claim 3, wherein:

said implantable lead comprises an elongated lead body for transvenous placement within a patient, the lead body having a distal end;

said electrode means comprises a tip and a ring electrode disposed at a distal end of said lead body, wherein said ring electrode comprises an interior chamber; and said accelerometer is disposed within said interior chamber of said ring electrode.

9. The implantable system of claim 8, wherein said ring electrode includes a first end and a second end, wherein said ring electrode further comprises:

a plug at said first end of said ring electrode and a hermetic feedthrough at said second end of said ring electrode for hermetically sealing said accelerometer within said ring electrode.

10. A method of detecting and discriminating among cardiac arrhythmias using a signal indicative of cardiac wall accelerations provided by a cardiac wall acceleration sensor delivered to a cardiac wall using an implantable lead, and for providing therapeutic electrical stimulation pulses to cardiac tissue in response to detected cardiac arrhythmias, said method comprising the steps of:

generating said signal indicative of cardiac wall acceleration;

analyzing said signal indicative of cardiac wall acceleration to detect and discriminate among cardiac arrhythmias;

generating said therapeutic electrical stimulation pulses in response to detected cardiac arrhythmias; and delivering said therapeutic electrical stimulation pulses to cardiac tissue using an electrode delivered to said cardiac tissue by said implantable lead.

11. The method of claim 10, wherein said cardiac wall acceleration sensor comprises a cantilever beam having a central axis, and said step of generating said signal indicative of cardiac wall acceleration comprises:

generating a signal indicative of accelerations of said cardiac wall along said central axis and perpendicular to said central axis.

12. The method of claim 11, further comprising the steps of:

sensing cardiac electrical activity to provide a signal indicative of said cardiac electrical activity; and detecting a cardiac arrhythmia using a primary indicating signal, said primary indicating signal being a selected one of said signal indicative of cardiac wall accelerations or said signal indicative of cardiac electrical activity.

13. The method of claim 12, further comprising the step of:

confirming a cardiac arrhythmia detected by said primary indicating signal using a secondary indicating signal, said secondary indicating signal being different from said primary indicating signal, said secondary indicating signal being a selected one of said signal indicative of cardiac wall accelerations or said signal indicative of cardiac electrical activity.

14. The implantable system of claim 5, wherein said accelerometer comprises:

a mounting surface attached to the electrode means;

a first cantilever beam having a free end, an end affixed to said mounting surface, and a planar surface, said first cantilever beam comprising a material having an electrical characteristic that varies measurably when a mechanical stress or strain is exerted on said material to provide said signal indicative of said accelerations; and a first mass disposed on said free end of said first cantilever beam for inducing a mechanical stress or strain in said material of said first cantilever beam when said first means is accelerated.

15. The implantable system of claim 14, wherein:

said first cantilever beam has a first and a second axis, said first axis extending from said fixed end to said free end of said first cantilever beam, said second axis being perpendicular to said planar surface of said first cantilever beam;

said first mass is disposed on said free end of said first cantilever beam so as to be offset with respect to said planar surface, so that a mechanical stress or strain is exerted on said material in response to accelerations along said first axis and in response to accelerations along said second axis; and said plurality of conductors comprises at least two wires for conducting said signal indicative of cardiac wall accelerations to said implantable cardiac stimulation device.

16. The implantable system of claim 5, wherein:

said electrode means includes a tip and a ring electrode;

said accelerometer has an output terminal and a ground terminal, said ground terminal being electrically connected to said ring electrode;

said plurality of conductors includes a first wire connected to said output terminal, and a second and third wire for connecting said tip and ring electrodes, respectively, said third wire being a shared wire between said ring electrode and said ground terminal of said accelerometer.

* * * * *